US011154250B2

(12) United States Patent
Han et al.

(10) Patent No.: US 11,154,250 B2
(45) Date of Patent: Oct. 26, 2021

(54) METHODS AND SYSTEMS FOR CALCULATING PHYSIOLOGICAL PARAMETERS

(71) Applicant: Shenzhen Mindray Bio-Medical Electronics Co., Ltd., Shenzhen (CN)

(72) Inventors: Fei Han, Shenzhen (CN); Fei Ye, Shenzhen (CN); Zuming Yao, Shenzhen (CN); Fei Zhang, Shenzhen (CN); Xianliang He, Shenzhen (CN); Lihan Liu, Shenzhen (CN); Ming Li, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 456 days.

(21) Appl. No.: 16/203,068

(22) Filed: Nov. 28, 2018

(65) Prior Publication Data

US 2019/0133535 A1 May 9, 2019

Related U.S. Application Data

(63) Continuation of application No. PCT/CN2016/085777, filed on Jun. 15, 2016.

(51) Int. Cl.
*A61B 5/00* (2006.01)
*A61B 5/02* (2006.01)
(Continued)

(52) U.S. Cl.
CPC .............. *A61B 5/7257* (2013.01); *A61B 5/00* (2013.01); *A61B 5/02* (2013.01); *A61B 5/024* (2013.01);
(Continued)

(58) Field of Classification Search
CPC ....... A61B 5/7257; A61B 5/02; A61B 5/1455; A61B 5/024; A61B 5/14551; A61B 5/7225; A61B 5/145
See application file for complete search history.

(56) References Cited

U.S. PATENT DOCUMENTS

| | | | |
|---|---|---|---|
| 2013/0172760 A1 | 7/2013 | Chon et al. | |
| 2014/0343385 A1 | 11/2014 | Baker, Jr. | |
| 2015/0105637 A1* | 4/2015 | Yu ..................... | A61B 5/14552 600/324 |

FOREIGN PATENT DOCUMENTS

| | | |
|---|---|---|
| CN | 1830386 A | 9/2006 |
| CN | 101039617 A | 9/2007 |

(Continued)

*Primary Examiner* — Eric F Winakur
*Assistant Examiner* — Abid A Mustansir
(74) *Attorney, Agent, or Firm* — Kory D. Christensen

(57) ABSTRACT

A method for calculating physiological parameters includes: selecting a section of time domain signal corresponding to at least one signal of red light and infrared light obtained by sampling, and performing a conversion from time domain to frequency domain to obtain a corresponding frequency domain signal; selecting all rational frequency spectrum peak information, calculating energy information of selected reasonable frequency spectrum peaks, and forming a frequency spectrum peak energy ratio sequence; constructing a stability coefficient according to the frequency spectrum peak energy ratio sequence, and if the stability coefficient is low, constructing a compensation coefficient by using the frequency spectrum peak energy ratio sequence; and compensating for at least one of the time domain signal and the frequency domain signal by using the compensation coefficient, and calculating based on at least one of the compensated time domain signal and the frequency domain signal to obtain the physiological parameters.

18 Claims, 15 Drawing Sheets

(51) Int. Cl.
*A61B 5/1455* (2006.01)
*A61B 5/024* (2006.01)

(52) U.S. Cl.
CPC ........ *A61B 5/1455* (2013.01); *A61B 5/14551* (2013.01); *A61B 5/7225* (2013.01)

(56) References Cited

FOREIGN PATENT DOCUMENTS

| | | |
|---|---|---|
| CN | 101103921 A | 1/2008 |
| CN | 201104882 Y | 8/2008 |
| CN | 103230267 A | 8/2013 |
| EP | 1611847 A1 | 4/2006 |
| JP | 201295940 A | 5/2012 |
| WO | WO 2009133851 A1 | 11/2009 |

\* cited by examiner

METHODS AND SYSTEMS FOR CALCULATING PHYSIOLOGICAL PARAMETERS

TECHNICAL FIELD

The present disclosure relates to the field of medical monitoring, in particular to methods and systems for calculating physiological parameters.

BACKGROUND

The metabolic process of the human body is a biological oxidation process. The oxygen required for the metabolic process enters the human blood through the respiratory system, where it is combined with reduced hemoglobin (Hb) in the red blood cells of the blood to form oxyhemoglobin (HbO2), which is then transported to tissue cells of various parts of the human body. When there is an imbalance between oxygen supply and oxygen consumption in the body, the patient is experiences hypoxia, which has a huge impact on the body. Accordingly, real-time monitoring of arterial blood oxygen concentration is very important in clinical care.

Blood oxygen saturation (SpO2) is the percentage of oxyhemoglobin (HbO2) capacity to the total hemoglobin (Hb+HbO2) capacity in the blood, i.e., the concentration of blood oxygen in the blood. As an indirect reflection of arterial blood oxygen saturation (SaO2), the blood oxygen saturation (SpO2) is used by various applications because of its non-invasiveness, simplicity, accuracy, and rapid calculation.

The application of pulse oximetry is so extensive that the accuracy requirement for pulse oximeters is also rising. As will be appreciated by those skilled in the art, there are two key factors in evaluating the pros and cons of the performance of the pulse oximetry: weak perfusion performance and movement performance. If the patient being tested has a poor weak perfusion performance or a poor movement performance, the accuracy and stability requirements for the performance of the pulse oximetry are more demanding.

Masimo has quickly established its leading position in the blood oxygen industry since pioneering a technique for an accurate measurement of patient blood oxygen saturation under movement and weak perfusion in 1998. The core idea of the technique is to establish coefficients Ra and Rv, where Ra is related to an arterial blood oxygen saturation and Rv is related to a venous blood oxygen saturation. By means of the R coefficients, infrared light and red light, a reference signal may be constructed. The energy of the reference signal is related to the coefficients. At the coefficients Ra and Rv, the maximum energy may be reached. Therefore, the coefficient of blood oxygen saturation from 0 to 100% is traversed, and the coefficients Ra and Rv are found to calculate the arterial blood oxygen saturation. This method requires a high amount of computation, and the hardware cost of implementing the same is relatively high.

Based on Lambert-Bear's law, the oxyhemoglobin (HbO2) and deoxyhemoglobin (HB) have different absorption characteristics in different light bands, as shown in FIG. 1, which is an oxyhemoglobin and reduced hemoglobin absorption spectrum curve; and the blood oxygen saturation parameter may be further evaluated by using the absorption characteristics.

As shown in FIG. 2, which is a working diagram of conventional blood oxygen measurement, a light emitting tube is configured to emit two beams of light (for example, red light and near-infrared light) for transmitting through body tissues, and a receiving tube is configured to receive light signals transmitted through the body tissues, so as to obtain the amount of blood pulsating component alternating current (AC) (for example, arterial blood) and the amount of non-pulsating component direct current (DC) (for example, venous blood, muscle, bone, skin, etc.). By using the amount of alternating current (AC) and the amount of direct current (DC) of red and near-infrared light respectively, the ratio of the mapping curve to the arterial blood oxygen saturation (SaO2), that is, a R coefficient table (as shown in Equation 1) may be obtained. The infinite approximation of pulse oxygen saturation (SpO2) of arterial blood oxygen saturation (SaO2) may then be obtained based on a look-up table method.

$$R = \frac{AC_{Red}/DC_{Red}}{AC_{Ired}/DC_{Ired}} \qquad \text{Equation 1}$$

where $AC_{Red}$=the amount of red light detected, i.e., the amount of alternating current; $DC_{Red}$=the maximum transmission amount of red light detected, i.e., the amount of direct current; $AC_{Ired}$=the amount of infrared light detected; and $DC_{Ired}$=the amount of direct current of infrared light detected.

However, how to accurately identify the AC and DC components in an acquired signal and obtain the accurate R values is not easy. Two conventional techniques are time domain technology and frequency domain technology.

The time domain technology has the characteristics of fast response speed and clear phase information. Since the time domain signal is a mixture of the useful signal and the noise signal, the noise outside a physiological bandwidth may be easily filtered by a high pass/low pass filter; whereas, when the noise within the physiological bandwidth occurs, due to the variability of the noise and lack of prior knowledge, the time domain method has almost no way to perform filtering processing on out this part of the noise. Therefore, the time domain technology has natural defects in anti-movement performance.

The frequency domain technology theoretically may separate the frequency bands of noise and useful signals, thereby achieving the purpose of distinguishing and identifying real signals. According to the definition of digital signal processing, any waveform is composed of multiple sinusoidal waves, and the pulse wave of a physiological parameter is no exception. Therefore, when the physiological pulse wave signal is converted into a frequency domain signal, the physiological parameter exhibits the fundamental and multiplied frequency characteristics. When interference occurs, the interference frequency spectrum and the fundamental and multiplied frequency spectrum of the physiological parameter are aliased together, and it is very difficult to identify which one is the true frequency spectrum. Therefore, although the frequency domain technology has advantages, it is also very difficult to accurately calculate the blood oxygen related parameter under an interference condition.

According to Parseval's theorem, the total energy of the time domain is equal to the total energy of the frequency domain of the signal. Therefore, Equation 1 is also applicable to the frequency domain signal, wherein the AC amount corresponds to the energy change at each frequency point. Under an ideal condition, after normalization, the red and infrared frequency spectrum of the pulse wave is as shown in FIG. 3, and the ratio of the main frequency band and various multiplied frequency bands may be regarded as the corresponding energy ratio in this frequency band. The meaning of the energy ratio is completely consistent with the meaning of the corresponding R values in Equation 1, that is, it corresponds uniquely to the blood oxygen saturation. In an ideal state without considering noise, the ratio of each frequency band is the same, which corresponds uniquely to the current blood oxygen saturation. In theory, the blood oxygen saturation parameter may be obtained in any frequency band.

Similarly, according to the composition theory of the signal, the frequency at which the fundamental frequency peak is located in FIG. 3 is the pulse rate value. The method of routinely detecting the fundamental frequency peak frequency may be obtained by identifying and screening the fundamental and multiplied frequency peaks, based on the theory that the fundamental frequency peak and the harmonic peak have a proportional relationship between energy and frequency. The physiological pulse rate value may be identified by means of this proportional relationship.

In summary, the pulse rate parameter and the blood oxygen parameter may be obtained by retrieving the position information about the fundamental and multiplied frequency peaks in the frequency domain signal and the energy ratios of the red light and the infrared light. However, in the case of interference, the information about the frequency spectrum peaks of the red light and the infrared light may be confused and annihilated by the noise, and the pulse rate may be incorrectly calculated due to the unrecognizable or misidentified fundamental frequency peak frequency information; and, at the same time, the energy ratios of the red light and the infrared light also result in that the blood oxygen calculation deviation is relatively large due to the mixing of noise. FIG. 4 is an illustration of the frequency spectrum distribution under interference is given. FIG. 4 shows that the frequency spectrum peak energy ratios of the infrared light and the red light are suddenly large and small, and the fundamental frequency peak is almost annihilated. In this case, it is almost impossible to correctly identify the frequency spectrum peak by using the existing time-frequency domain technology and calculate the accurate blood oxygen and pulse rate parameters.

SUMMARY

The embodiments of the present disclosure solve the aforementioned problem, improving the calculation accuracy for the physiological parameter (such as the pulse rate value and the blood oxygen parameter) under weak irrigation and movement conditions, while maintaining a low computational complexity and a low demand for computing resources.

One embodiment provides a method for calculating a physiological parameter, including: selecting a section of a time domain signal corresponding to at least one signal of red light and infrared light obtained by sampling, and performing a time-to-frequency domain transformation on the section of the time domain signal to obtain a corresponding frequency domain signal; selecting all rational frequency spectrum peaks from the frequency domain signal, calculating energy information of the selected rational frequency spectrum peaks, and forming a frequency spectrum peak energy ratio sequence; constructing a stability coefficient according to the frequency spectrum peak energy ratio sequence, and if the stability coefficient is relatively low, constructing a compensation coefficient by using the frequency spectrum peak energy ratio sequence; and compensating for at least one of the time domain signal and the frequency domain signal by using the compensation coefficient, and calculating the physiological parameter based on at least one of the compensated time domain signal and frequency domain signal.

In another aspect of the present disclosure, a system for calculating a physiological parameter includes: a sensor comprising at least one light emitting tube and at least one receiving tube, the light emitting tube emitting at least two optical signals of different wavelengths for transmitting through a physiological tissue, and the receiving tube receiving the at least two optical signals transmitted through the physiological tissue and converting the at least two optical signals received into electrical signals; an analog to digital converter connected to the sensor to convert the electrical signals into digital signals, the digital signals include at least some of the characteristics of the physiological tissue; a digital processor connected to the analog to digital converter.

In one embodiment, the digital processor: performs a time-to-frequency domain transformation on a section of the digital signal to obtain a corresponding frequency domain signal; (b) selects all rational frequency spectrum peaks from the frequency domain signal, calculates energy information of the selected rational frequency spectrum peaks, and forms a frequency spectrum peak energy ratio sequence; (c) constructs a stability coefficient according to the frequency spectrum peak energy ratio sequence, and if the stability coefficient is relatively low, constructs a compensation coefficient by using the frequency spectrum peak energy ratio sequence; and (d) compensates for at least one of the time domain signal and the frequency domain signal by using the compensation coefficient, and calculates the physiological parameter based on at least one of the compensated digital signal and frequency domain signal.

In one embodiment, a method for calculating a physiological parameter includes: selecting a section of a time domain signal corresponding to at least one signal of red light and infrared light obtained by sampling, and performing a time-to-frequency domain transformation on the section of the time domain signal to obtain at least one frequency domain signal; selecting all rational frequency spectrum peaks from the frequency domain signal, calculating position information of the selected rational frequency spectrum peaks, and forming a frequency spectrum peak position sequence; constructing a time-varying array map according to the frequency spectrum peak position sequence, and constructing at least one stability factor for each position point that varies over time to form a stability factor array map; constructing a stability coefficient based on the stability factor array map, and if the stability coefficient is relatively low, calculating a compensation coefficient by using the stability factor array map; and compensating for at least one of the time domain signal and the frequency domain signal by using the compensation coefficient, and calculating the physiological parameter based on at least one of the compensated time domain signal and frequency domain signal.

A system for calculating a physiological parameter may include: a sensor comprising at least one light emitting tube and at least one receiving tube, the light emitting tube emitting at least two optical signals of different wavelengths for transmitting through a physiological tissue, and the receiving tube receiving the at least two optical signals transmitted through the physiological tissue and converting the at least two optical signals received into electrical signals; an analog to digital converter connected to the sensor to convert the electrical signals into digital signals, the digital signals include at least some of the characteristics of the physiological tissue; a digital processor connected to the analog to digital converter. In one embodiment, the digital processor performs the following processes: performing a time-to-frequency domain transformation on a section of the digital signal to obtain a corresponding frequency domain signal; selecting all rational frequency spectrum peaks, calculating position information of the selected rational frequency spectrum peaks, and forming a frequency spectrum peak position sequence; constructing a time-varying array map according to the frequency spectrum peak position sequence, and constructing at least one stability factor for each position point that varies over time to form a stability factor array map; constructing a stability coefficient based on the stability factor array map, and if the stability coefficient is relatively low, calculating a compensation coefficient by using the stability factor array map; and compensating for at least one of the time domain signal and the frequency domain signal by using the compensation coefficient, and calculating the physiological parameter based on at least one of the compensated digital signal and frequency domain signal.

In an aspect of the present disclosure, a method for calculating a physiological parameter includes: selecting a section of a time domain signal corresponding to at least one signal of red light and infrared light obtained by sampling, and performing a time-to-frequency domain transformation on the section of the time domain signal to obtain at least one frequency domain signal; selecting all rational frequency spectrum peaks from the frequency domain signal, calculating at least one of energy and position information of the selected rational frequency spectrum peaks, and forming at least one of a frequency spectrum peak energy ratio sequence and a frequency spectrum peak position sequence; constructing a stability coefficient according to at least one of the frequency spectrum peak energy ratio sequence and the frequency spectrum peak position sequence, and if the stability coefficient is relatively low, constructing a compensation coefficient by using at least one of the frequency spectrum peak energy ratio sequence and the frequency spectrum peak position sequence; and compensating for at least one of the time domain signal and the frequency domain signal by using the compensation coefficient, and calculating the physiological parameter based on at least one of the compensated time domain signal and frequency domain signal.

In one embodiment, a system for calculating a physiological parameter, includes: a sensor comprising at least one light emitting tube and at least one receiving tube, the light emitting tube emitting at least two optical signals of different wavelengths for transmitting through a physiological tissue, and the receiving tube receiving the at least two optical signals transmitted through the physiological tissue and converting the at least two optical signals received into electrical signals; an analog to digital converter connected to the sensor to convert the electrical signals into digital signals, the digital signals include at least some of the characteristics of the physiological tissue; a digital processor connected to the analog to digital converter. In one embodiment, the digital processor performs the following processes: performing a time-to-frequency domain transformation on a section of the digital signal to obtain a corresponding frequency domain signal; selecting all rational frequency spectrum peaks from the frequency domain signal, calculating at least one of energy and position information of the selected rational frequency spectrum peaks, and forming at least one of a frequency spectrum peak energy ratio sequence and a frequency spectrum peak position sequence; constructing a stability coefficient according to at least one of the frequency spectrum peak energy ratio sequence and the frequency spectrum peak position sequence, and if the stability coefficient is relatively low, constructing a compensation coefficient by using at least one of the frequency spectrum peak energy ratio sequence and the frequency spectrum peak position sequence; and compensating for at least one of the time domain signal and the frequency domain signal by using the compensation coefficient, and calculating the physiological parameter based on at least one of the compensated digital signal and frequency domain signal.

The embodiments of the present disclosure have several advantages.

First, embodiments of present disclosure are based on the frequency domain technology combined with the time domain technology, which may greatly improve the calculation accuracy of the physiological parameter under weak perfusion and patient movement, greatly improving the calculation accuracy the physiological parameter (such as the blood oxygen parameter);

Second, the embodiments of present disclosure combine the characteristics of time and frequency domain signals with the characteristics of the human physiological parameter, the venous oxygen compensation method and the power spectrum array method are used in the case of interference, so as to improve the accuracy of calculating the physiological parameter (such as the pulse rate value and the blood oxygen parameter) under weak irrigation and movement conditions. The venous oxygen compensation method may eliminate the measurement deviation of blood oxygenation caused by interference, infinitely approach the true physiological blood oxygen value, and greatly provide the accuracy of the calculation of the blood oxygen parameter under the interference condition. The power spectrum array method may eliminate the measurement deviation of the pulse rate caused by interference, may accurately identify the physiological frequency spectrum information even under the long-term interference condition, and greatly provides the accuracy of the calculation of the pulse rate parameter under the interference condition.

In addition, the methods provided in the embodiments of the present disclosure have a low computational complexity and low demand for computing resources.

DETAILED DESCRIPTION

The present disclosure is further illustrated in detail below in conjunction with the accompanying drawings. It should be understood that the particular embodiments described herein are intended to be illustrative and not limiting.

Figure 5:
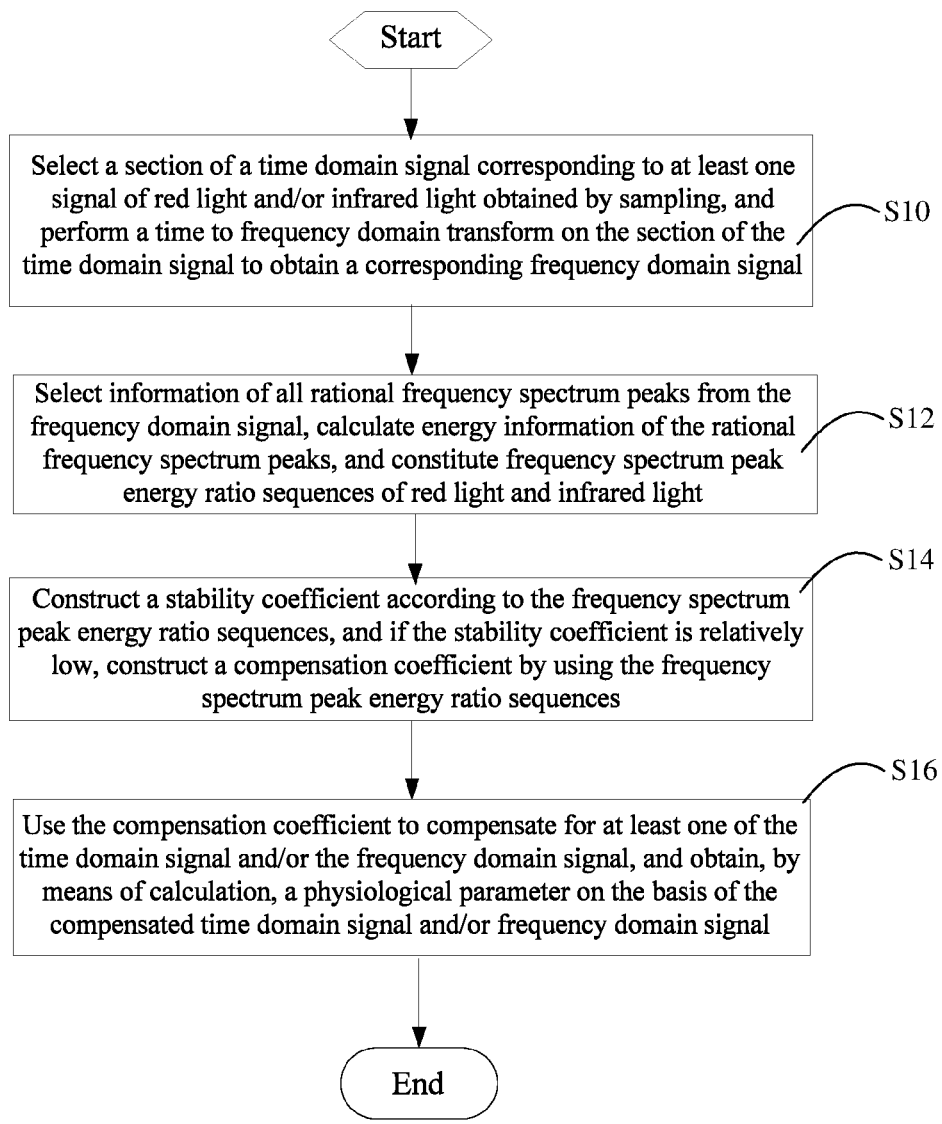
FIG. 5 is a flow chart of a method for calculating a physiological parameter.

FIG. 5 is a flow chart of a method for calculating the accuracy of a physiological parameter provided by the present disclosure. In this embodiment, the compensation process of a venous oxygen compensation (VOC) method is shown including the following steps:

Step S10: Selecting a section of a time domain signal corresponding to at least one signal of red light and infrared light obtained by sampling, and performing a time-to-frequency domain transformation on the section of the time domain signal to obtain a corresponding frequency domain signal;

Step S12: Selecting information about all rational frequency spectrum peaks from the frequency domain signal, calculating energy information of the selected rational frequency spectrum peaks, and forming frequency spectrum peak energy ratio sequences of red light and infrared light, wherein the information about the rational frequency spectrum peaks satisfies at least one of a frequency spectrum energy relationship (e.g., whether there is a fundamental and multiplied frequency relationship), a frequency spectrum amplitude relationship (e.g., whether the amplitude is not lower than a fixed value), a frequency spectrum positional relationship, a frequency spectrum peak morphological relationship (e.g., whether the shape of the frequency spectrum peak is bilaterally symmetric about a frequency point) and other factors; and Step S14: Constructing a stability coefficient according to the frequency spectrum peak energy ratio sequences, and if the stability coefficient is relatively low, constructing a compensation coefficient by using the frequency spectrum peak energy ratio sequences, wherein the stability coefficient is constructed based on deviation statistics for energy ratios of the red light and the infrared light or based on deviation statistics for blood oxygen parameter values, or is an empirical coefficient. The empirical coefficient is abstracted according to the physiological state and the signal-to-noise ratio characteristics. As an example, when a movement interference is identified, the physiological blood oxygen may not be too low; under long-term movement, the physiological blood oxygen will have a downward trend; and when the movement interference is severe and the noise component is much larger than the signal component, the blood oxygen approaches 80%, and so on. Combined with the blood oxygen system, a digital empirical coefficient value may be formed. Specifically, the stability coefficient is compared with a set threshold to determine whether the stability coefficient is relatively low. In one example, information about a mean value, a standard deviation, a maximum value, and a minimum value of a statistical spectrum peak energy ratio deviation sequence or blood oxygen deviation sequence may be used to obtain the stability coefficient according to a specific algorithm.

As an example, the following method may be used to construct the compensation coefficient:

selecting the mean value of the physiological parameter (such as the blood oxygen parameter) to be the denominator input source of a compensation coefficient calculation formula; selecting (the mean value+the standard deviation) or (the mean value−the standard deviation) to be the numerator input source of the compensation coefficient calculation formula; and calculating the corresponding compensation coefficient by substituting the numerator input source and the denominator input source into the following compensation coefficient calculation formula:

$$\text{Factor}_{compensation} = \text{tab}R(\text{Numerator})/\text{tab}R(\text{Denominator})$$

where tabR(Numerator) is a R coefficient value obtained by looking up a mapping table of a predetermined blood oxygen and R curve coefficient with the numerator input source being the blood oxygen value, and tabR(Denominator) is a R coefficient value obtained by looking up a mapping table of a predetermined blood oxygen and R curve coefficient with the denominator input source being the blood oxygen value; and $\text{Factor}_{compensation}$ is the complement coefficient.

Step S16: Compensating for at least one of the time domain signal and the frequency domain signal by using the compensation coefficient, and calculating the physiological parameter based on at least one of the compensated time domain signal and frequency domain signal, wherein the physiological parameter is at least one of blood oxygen, pulse rate, waveform area, and perfusion index.

Taking the physiological parameter being the blood oxygen saturation parameter as an example below, a further detailed flowchart in FIG. 5 is illustrated.

First, in step S10, a section of a time domain signal is selected, which corresponds to at least one signal of red light and infrared light obtained by sampling, and a time-to-frequency domain transformation is performed on the section of the time domain signal to obtain a corresponding frequency domain signal;

Next, in step S12, information about all rational frequency spectrum peaks is selected from the frequency domain signal, energy information about the selected rational frequency spectrum peaks is calculated, and forms the frequency spectrum peak energy ratio sequences of the red light and the infrared light, specifically, the blood oxygen distribution sequence is statistically analyzed according to the blood oxygen saturation parameter of each of the rational frequency spectrum peaks, to obtain a plurality of pieces of characteristic information, and specifically, at least the mean value vMean, the standard deviation vStd, the maximum value vMax, and the minimum value vMin of the blood oxygen saturation are calculated according to the blood oxygen saturation parameter of each of the rational frequency spectrum peaks; and Finally, in step S14, a stability coefficient is constructed according to the frequency spectrum peak energy ratio sequence, and if the stability coefficient is relatively low, a compensation coefficient is constructed by using the frequency spectrum peak energy ratio sequences. Specifically, in the plurality of pieces of characteristic information obtained in the foregoing step, a difference between the maximum value and the minimum value is used as the stability coefficient, and if the stable system is less than or equal to a set first threshold, the stability coefficient is determined to be relatively low, and there is a need to construct a compensation coefficient.

In some embodiments, the process of constructing the compensation coefficient may be obtained by the following method:

if the standard deviation vStd is less than a preset second threshold at this point, selecting the mean value to be the denominator input source of the compensation coefficient calculation formula; if the number of blood oxygens exceeding the mean value in the blood oxygen sequence accounts for at least half of the total number of the sequence, using the maximum value+the standard deviation as the numerator input source of the compensation coefficient calculation formula, otherwise using the maximum value–the standard deviation as the numerator input source of the compensation coefficient calculation formula;

if the standard deviation is greater than the preset second threshold value, obtaining a repetition factor is obtained in a predetermined manner and using same as the numerator input source of the compensation coefficient calculation formula, and using the mean value as the denominator input source of the compensation coefficient calculation formula; and calculating the corresponding compensation coefficient by substituting the numerator input source and the denominator input source into the following compensation coefficient calculation formula:

$$\text{Factor}_{compensation} = \text{tab}R(\text{Numerator})/\text{tab}R(\text{Denominator}) \quad \text{Formula 1}$$

where tabR(Numerator) is a R coefficient value obtained by looking up a mapping table of a predetermined blood oxygen and R curve coefficient with the numerator input source being the blood oxygen value, and tabR(Denominator) is a R coefficient value obtained by looking up a mapping table of a predetermined blood oxygen and R curve coefficient with the denominator input source being the blood oxygen value; and $\text{Factor}_{compensation}$ is the complement coefficient.

The step of obtaining the repetition factor in a predetermined manner may include:

obtaining a maximum blood oxygen parameter set satisfying a certain deviation value (e.g., +2%) in the statistical blood oxygen distribution sequence, and calculating the mean value of the maximum blood oxygen parameter set as the repetition factor; or selecting a stable segment within a certain time range (e.g., 4 s-8 s) in the historical trend of blood oxygen, and calculating the mean value of the blood oxygen parameter set in the stable segment as the repetition factor; and finally, in step S16, the compensation coefficient is used to compensate for the time domain signal corresponding to at least one of the red light and the infrared light, and the physiological parameter is further calculated by using at least one of the compensated time domain signal. The physiological parameter is at least one of a blood oxygen parameter, a pulse rate parameter, a waveform area parameter, and a perfusion index parameter. Specifically, the following two methods may be used:

I. according to the compensated time domain signal, the final blood oxygen saturation parameter and the pulse rate value are calculated according to a time domain algorithm; or II. a time-to-frequency domain transformation is performed on the compensated time domain signal to obtain a frequency domain signal, and a rational frequency spectrum peak is selected from the frequency domain signal, and the rational frequency spectrum peak is calculated according to a frequency domain algorithm to obtain an accurate final blood oxygen saturation parameter.

Figure 6:
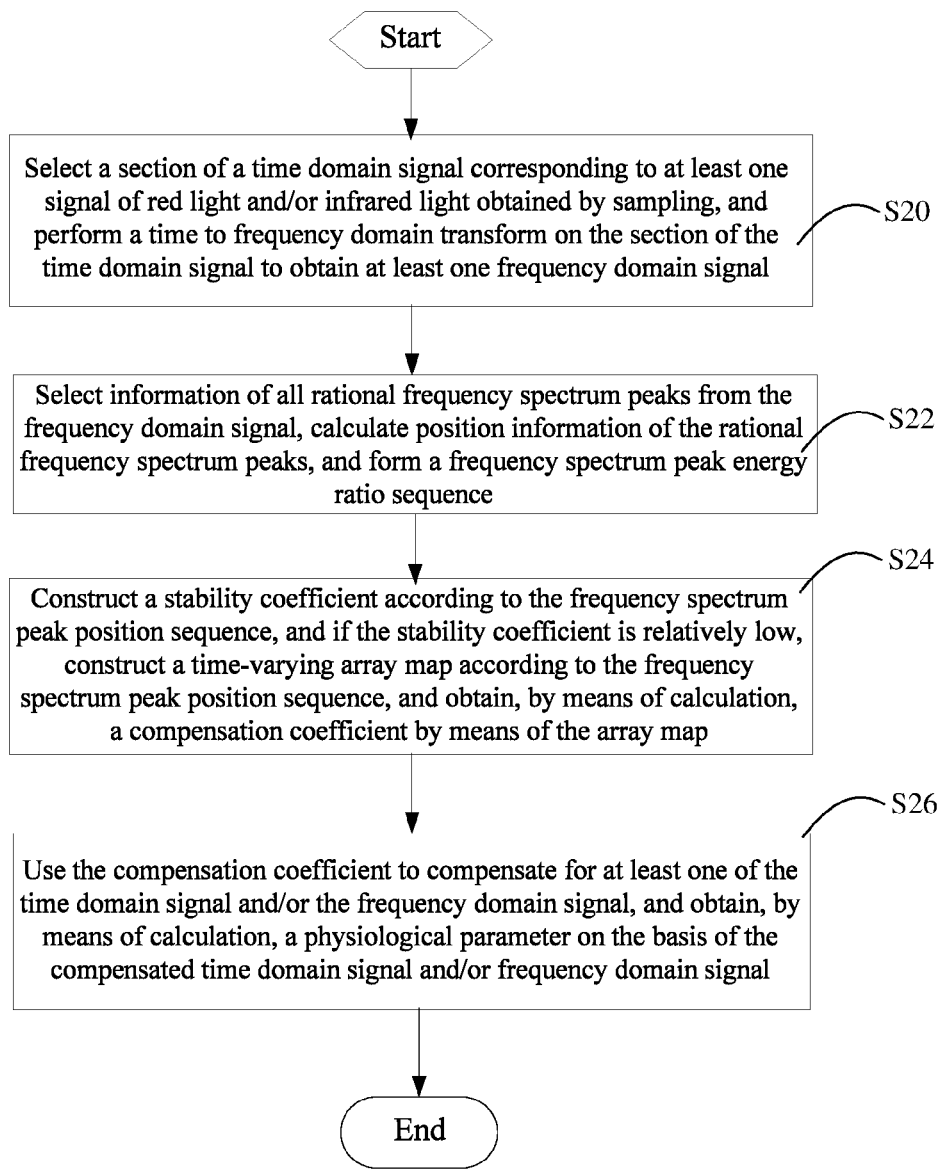
FIG. 6 is a another flow chart of a method for calculating a physiological parameter.

As shown in FIG. 6, which shows a schematic diagram of a main process of another embodiment of a method for calculating the accuracy of a physiological parameter provided by the present disclosure, in this embodiment, the compensation process of a power spectrum array (PSA) method is shown including the following steps:

Step S20: Selecting a section of a time domain signal corresponding to at least one signal of red light and infrared light obtained by sampling, and performing a time-to-frequency domain transformation on the section of the time domain signal to obtain at least one frequency domain signal;

Step S22: Selecting information about all rational frequency spectrum peaks from the frequency domain signal, calculating position information of the selected rational frequency spectrum peaks, and forming a frequency spectrum peak position sequence, wherein the information about the rational frequency spectrum peaks satisfies at least one or more of a frequency spectrum energy relationship, a frequency spectrum amplitude relationship, a frequency spectrum positional relationship, and a frequency spectrum peak morphological relationship;

Step S24: Constructing a stability coefficient according to the frequency spectrum peak position sequence, and if the stability coefficient is relatively low, constructing a time-varying array map according to the frequency spectrum peak position sequence, and calculating a compensation coefficient by means of the array map, wherein the stability coefficient is constructed based on at least one of a frequency spectrum energy ratio deviation, a frequency spectrum blood oxygen deviation, a state of a fundamental and multiplied frequency group, and a number of rational frequency spectrum peaks, and whether the stability coefficient is relatively low may be determined according to at least one of a number of stability factors and weight values.

In an example, the stability coefficient is determined according to the state of the fundamental and multiplied frequency group in the frequency spectrum peak position sequence; for example, when a pair of fundamental and multiplied frequency groups are not identified in the frequency spectrum peak position sequence, the stability coefficient is considered to be relatively low.

Specifically, the step of constructing the time-varying array map according to the frequency spectrum peak position sequence, and calculating the compensation coefficient by means of the array map includes: establishing a cache to store information about the frequency spectrum peaks, which information includes: each frequency spectrum peak position information PeakArray; each frequency spectrum peak position weight information WeigtedArray; and information about the number of frequency spectrum peaks stored ArrayIndex;

Step S161: Screening a predetermined number of frequency spectrum peaks in the frequency domain signal, sequentially filling same into the cache, writing the position information about each frequency spectrum peak into the PeakArray, incrementing the corresponding position weight in the WeigtedArray, and incrementing the total length ArrayIndex, wherein, if the currently screened frequency spectrum peak is the same as a frequency spectrum peak in the cache, the position weight information WeigtedArray of the frequency spectrum peak in the cache is directly incremented.

Step S162: In the cache, assuming each frequency spectrum peak as a suspected fundamental frequency peak, traversing all the other frequency spectrum peaks, determining whether the other frequency spectrum peaks and the suspected fundamental frequency peak satisfy a frequency multiplication relationship, and if so, eliminating the information about the multiplied frequency peaks in the cache, and the position weight coefficients of the multiplied frequency peaks are converted according to the frequency multipliers and added to the position weight coefficient of the corresponding suspected fundamental frequency peak; otherwise, remaining the information about the other frequency spectrum peaks;

Step S163: Selecting three frequency spectrum peaks, position weight coefficients of which are ranked in the front in the last suspected frequency spectrum peak, determining one of them to be the final rational frequency spectrum peak (in some examples, which may be considered as a fundamental frequency peak), and obtaining the pulse rate value according to the determined final frequency spectrum peak; similarly, it may be understood that the corresponding blood oxygen saturation may be obtained, by means of energy calculation, according to the final rational frequency spectrum peak.

Specifically, the step further includes: comparing the position weight coefficient of each of the selected frequency spectrum peaks with a predetermined third threshold; if the number of frequency spectrum peaks, the position weight coefficient of which is greater than the third threshold, is one, determining the frequency spectrum peak to be the final rational frequency spectrum peak; and if the number of frequency spectrum peaks, the position weight coefficient of which is greater than the third threshold, is at least two, determining one of the frequency spectrum peaks to be the final rational frequency spectrum peak, and using information about the later final rational frequency spectrum peak as the compensation coefficient.

Step S26: Compensating for at least one of the time domain signal and the frequency domain signal by using the compensation coefficient, and calculating the physiological parameter based on at least one of the compensated time domain signal and frequency domain signal, wherein the physiological parameter is at least one of blood oxygen, pulse rate, waveform area, and perfusion index, and wherein in an example, the use of the compensation coefficient to compensate for at least one of the time domain signal and the frequency domain signal may be specifically: constructing a band pass filter according to the compensation coefficient, and filtering at least one of the time domain signal and the frequency domain signal to achieve compensation function.

Figure 7:
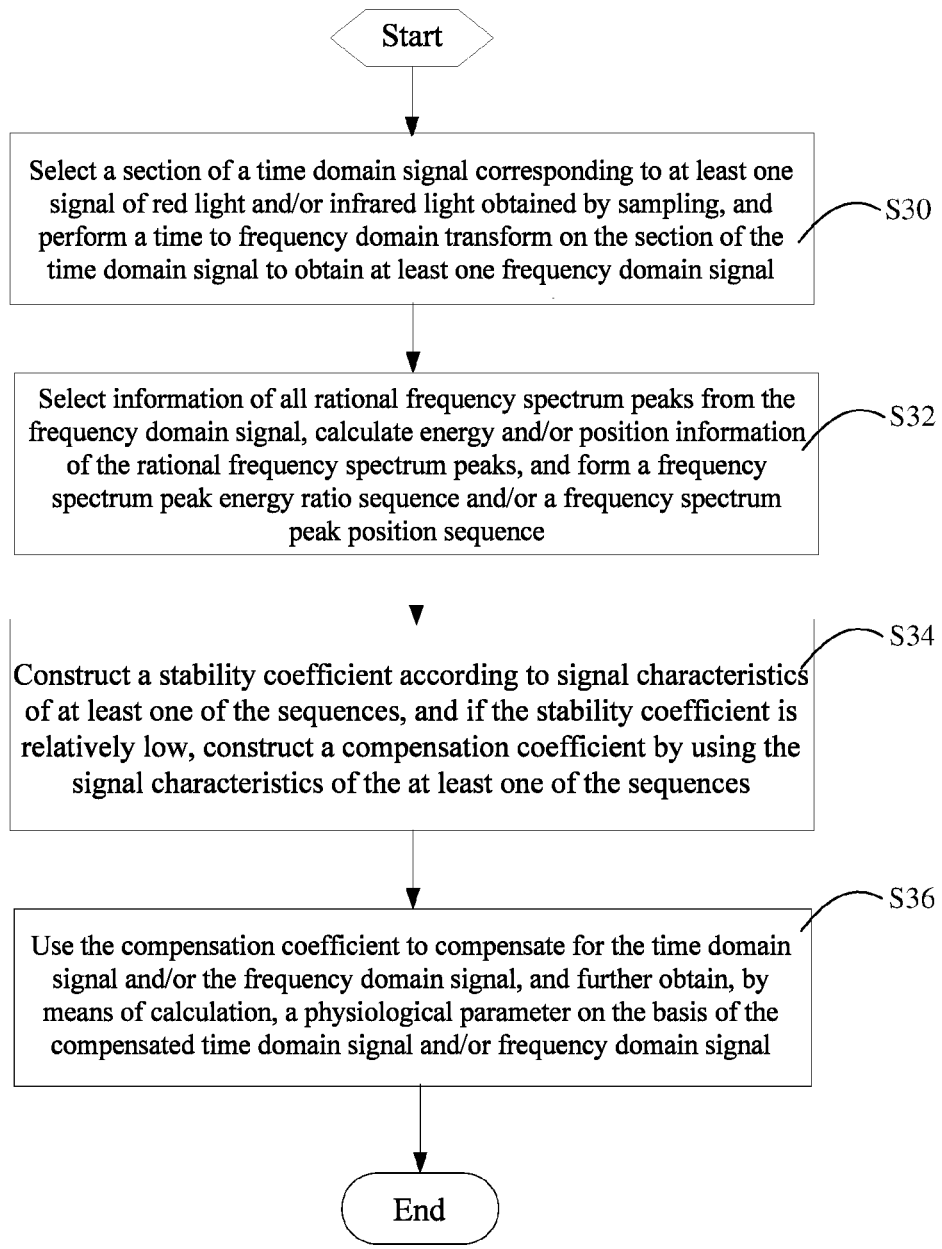
FIG. 7 is a yet another flow chart of a method for calculating a physiological parameter.

FIG. 7 is a flowchart of a method for calculating the accuracy of a physiological parameter. In this embodiment, a venous oxygen compensation (VOC) method and a power spectrum array (PSA) method are combined in the compensation process. In one embodiment, the method includes the following steps:

Step S30 Selecting a section of a time domain signal corresponding to at least one signal of red light and infrared light obtained by sampling, and performing a time-to-frequency domain transformation on the section of the time domain signal to obtain at least one frequency domain signal;

Step S32: Selecting information about all rational frequency spectrum peaks from the frequency domain signal, calculating at least one of energy and position information of the selected rational frequency spectrum peaks, and forming a frequency spectrum peak energy ratio sequence and a frequency spectrum peak position sequence, wherein the information about the rational frequency spectrum peaks satisfies at least one or more of a frequency spectrum energy relationship, a frequency spectrum amplitude relationship, a frequency spectrum positional relationship, and a frequency spectrum peak morphological relationship, and the process of forming the frequency spectrum peak energy ratio sequence and the frequency spectrum peak position sequence may be respectively referred to the foregoing description of Step S12 in FIG. 5 and Step S22 in FIG. 6;

Step S34: Constructing a stability coefficient according to signal characteristics of at least one of the frequency spectrum peak energy ratio sequence and the frequency spectrum peak position sequence, and at the same time, determining whether the stability coefficient of at least one of the sequences is relatively low, and if the stability coefficient is relatively low, constructing a compensation coefficient by using the signal characteristics of the at least one of the sequences, wherein the stability coefficient is constructed based on at least one of a frequency spectrum energy ratio deviation, a frequency spectrum blood oxygen deviation, a state of a fundamental and multiplied frequency group, and a number of rational frequency spectrum peaks; and the compensation coefficient is an energy ratio deviation coefficient or a blood oxygen deviation coefficient calculated based on the frequency spectrum peak energy ratio sequence, or a position coefficient statistically obtained over time based on the frequency spectrum peak position sequence.

The specific process of constructing the stability coefficient according to the frequency spectrum peak energy ratio sequence, and constructing the compensation coefficient may be referred to the foregoing description of step S14 in FIG. 5; and the specific process of constructing the stability coefficient according to the frequency spectrum peak position sequence, and constructing the compensation coefficient may be referred to the foregoing description of step S24 in FIG. 6, so that they will not be described in detail herein.

Step S36: Compensating for at least one of the time domain signal and the frequency domain signal by using the compensation coefficient, and further calculating the physiological parameter based on at least one of the compensated time domain signal and frequency domain signal, wherein the physiological parameter is at least one or more of blood oxygen, pulse rate, waveform area, and perfusion index.

Specifically, the step includes at least one of the following: using the compensation coefficient to perform a gain processing on the selected time domain signal to achieve compensation; or using the compensation coefficient to perform filtering processing on the selected frequency domain signal to achieve compensation.

The present disclosure further provides a system for calculating a physiological parameter.

It will be understood that the method for calculating a physiological parameter disclosed by the present disclosure may be implemented by means of functional modularization, and integrated as a plug-in into other auxiliary diagnostic devices (such as a monitoring device, a defibrillator, an AED, an automatic resuscitation instrument, an electrocardiograph, etc.), or may be made as a single-parameter medical system for monitoring a related physiological parameter, wherein the physiological parameter includes at least one of a blood oxygen parameter, a pulse rate parameter, a waveform area parameter, and a perfusion index parameter.

Figure 21:
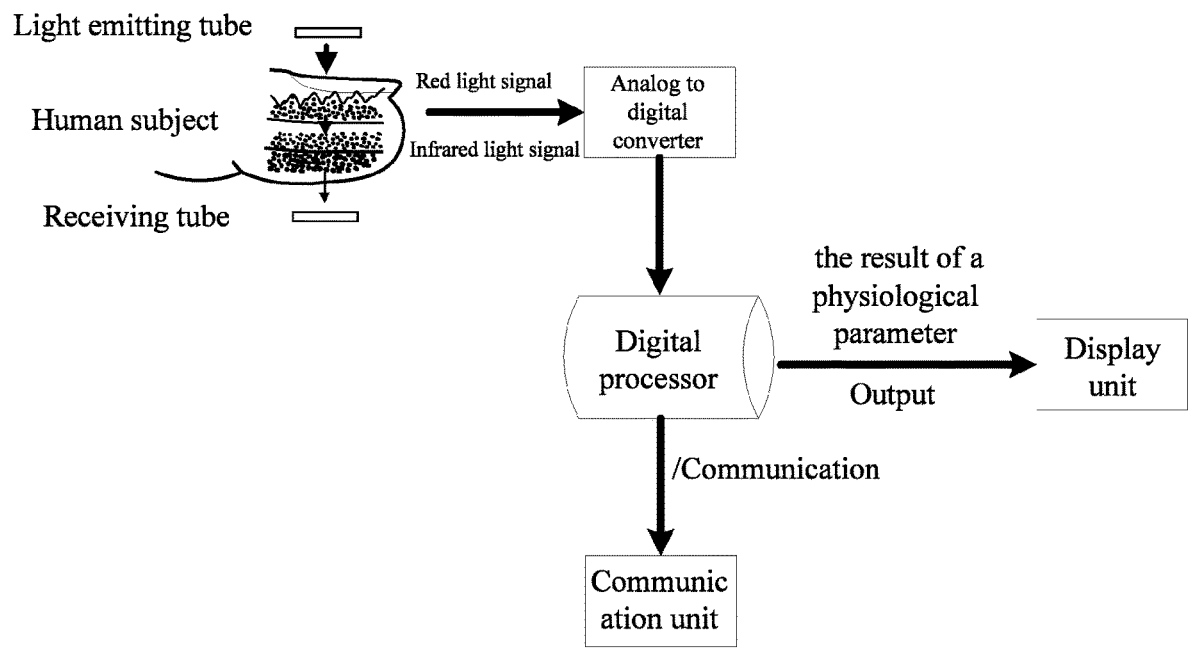
FIG. 21 is a schematic structural diagram of a system for calculating a physiological parameter.

FIG. 21 is a schematic structural diagram of a single-parameter medical system disclosed in the present disclosure including:

at least one blood oxygen sensor for measuring a part of a human subject, such as a finger, a forehead, an earlobe, a toe, and a sole. The blood oxygen sensor includes at least a light emitting tube and a receiving tube, and the light emitting tube is configured to emit at least two optical signals of different wavelengths for transmitting through a body tissue of the human subject. In an example, the light emitting tube may emit a red light signal and an infrared light signal. The receiving tube receives the at least two optical signals transmitted through the body tissue of the human subject and converts same into at least two electrical signals. In an example, the two electrical signals are a red light signal and an infrared light signal;

an analog to digital converter connected to the sensor to convert the electrical signals into digital signals, the digital signals include at least some of the characteristics of the physiological tissue;

a digital processor connected to the analog to digital converter, the digital processor performing the following processes:

performing a time-to-frequency domain transformation on a section of the digital signal to obtain a corresponding frequency domain signal;

selecting all rational frequency spectrum peaks from the frequency domain signal, calculating energy information of the selected rational frequency spectrum peaks, and forming a frequency spectrum peak energy ratio sequence;

constructing a stability coefficient according to the frequency spectrum peak energy ratio sequence, and if the stability coefficient is relatively low, constructing a compensation coefficient by using the frequency spectrum peak energy ratio sequence; and compensating for at least one of the time domain signal and the frequency domain signal by using the compensation coefficient, and calculating the physiological parameter based on at least one of the compensated digital signal and frequency domain signal.

Further, the system includes:

a display unit connected to the digital processor to display the physiological parameter calculated by the digital processor; and/or a communication unit connected to the digital processor to send the physiological parameter calculated by the digital processor. The aforementioned units, as well as the units described hereafter, may be implemented using any suitable combination of hardware, software, and/or firmware, and may contain custom or off-the-shelf components that implement the described functionality. In some embodiments, the units may be implemented, at least partially, by a general purpose processor executing instructions stored in a non-transitory computer-readable medium, such as a memory device (e.g, RAM, ROM, hard drive).

The blood oxygen sensor may be transmissive and/or reflective, and may be generally worn on a part of the human subject, such as the finger, the forehead, the earlobe, the toe and the sole, for measuring a physiological parameter comprising at least one of a blood oxygen parameter, a pulse rate parameter, a waveform area parameter, and a perfusion index parameter. The display unit may be a local display unit (e.g., computer monitor), or may be remotely communicated to a remote display unit in a wired/wireless manner. The display unit provides the user with a perceptible parameter representation by means of characters, values, waveforms, bar graphs, voice prompts, etc.

In one embodiment, the at least some of the characteristics of the physiological tissue is one or more of the optical characteristics of oxygenated hemoglobin, deoxyhemoglobin, methemoglobin, total hemoglobin and carbon monoxide in the blood.

In one embodiment, the rational frequency spectrum peaks satisfy at least one of a frequency spectrum energy relationship, a frequency spectrum amplitude relationship, a frequency spectrum positional relationship, and a frequency spectrum peak morphological relationship.

In one embodiment, the stability coefficient is constructed based on deviation statistics for energy ratios of the red light and the infrared light, or is an empirical coefficient.

In one embodiment, the stability factor adjusts a stability weight thereof over time according to at least one of the characteristics of a fundamental and multiplied frequency group and a frequency spectrum peak morphological rationality.

In one embodiment, the process of constructing, by the digital processor, the compensation coefficient by using the frequency spectrum peak energy ratio sequence may include: selecting the mean value and converting same by means of a coefficient table to a denominator of a compensation coefficient calculation formula, and selecting (the mean value+the standard deviation) or (the mean value−the standard deviation) and converting same by means of a coefficient table to a numerator of the compensation coefficient calculation formula, and calculating a ratio of the numerator to the denominator to obtain the compensation coefficient.

In one embodiment, the physiological parameter is at least one of blood oxygen, pulse rate, waveform area, perfusion index, etc.

In order to better understand the function of the digital processor in this embodiment, the following will be described in conjunction with a specific example.

Figure 8:
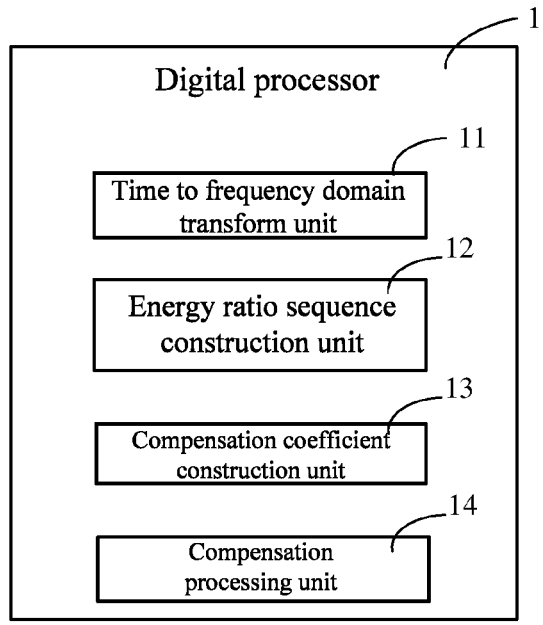
FIG. 8 is a schematic structural diagram a digital processor used in a system for calculating a physiological parameter.
Figure 9:
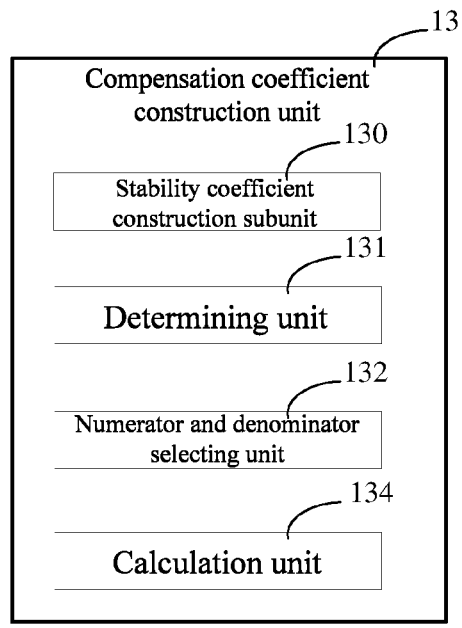
FIG. 9 is a schematic structural diagram of a compensation coefficient construction unit in FIG. 8.

As shown in FIG. 8, which shows a schematic structural diagram of an embodiment of a digital processor used in a system for calculating a physiological parameter, the digital processor uses a venous oxygen compensation (VOC) method for compensation. Reference is also made to FIG. 9, where the digital processor is illustrated as including:

a time-to-frequency domain transformation unit 11 for selecting a section of a time domain signal corresponding to at least one signal of red light and infrared light obtained by sampling, and performing a time-to-frequency domain transformation on the section of the time domain signal to obtain a corresponding frequency domain signal;

an energy ratio sequence construction unit 12 for selecting information about all rational frequency spectrum peaks from the frequency domain signal, calculating energy information of the selected rational frequency spectrum peaks, and forming frequency spectrum peak energy ratio sequences of red light and infrared light, wherein the information about the rational frequency spectrum peaks satisfies at least one of a frequency spectrum energy relationship, a frequency spectrum amplitude relationship, a frequency spectrum positional relationship, and a frequency spectrum peak morphological relationship;

a compensation coefficient construction unit 13 for constructing a stability coefficient according to the frequency spectrum peak energy ratio sequences, and if the stability coefficient is relatively low, constructing a compensation coefficient by using the frequency spectrum peak energy ratio sequence, wherein the stability coefficient is constructed based on deviation statistics for energy ratios of the red light and the infrared light or based on deviation statistics for blood oxygen parameter values, or is an empirical coefficient; and the stability coefficient is compared with a set threshold to determine whether the stability coefficient is relatively low; and a compensation processing unit 14 for using the compensation coefficient to compensate for the time domain signal corresponding to at least one of the red light and the infrared light, and further calculating the physiological parameter by using at least one of the compensated time domain signal.

The compensation coefficient construction unit 13 may further include:

a stability coefficient construction subunit 130 for using information about a mean value, a standard deviation, a maximum value, and a minimum value of a statistical spectrum peak energy ratio deviation sequence or blood oxygen deviation sequence to obtain the stability coefficient according to a specific algorithm;

a determining unit 131 for determining whether the stability coefficient constructed by the stability coefficient construction subunit 130 is relatively low;

a numerator and denominator selecting unit 132 for selecting the mean value of the physiological parameter (such as the blood oxygen parameter) to be the denominator input source of a compensation coefficient calculation formula; and selecting (the mean value+the standard deviation) or (the mean value−the standard deviation) to be the numerator input source of the compensation coefficient calculation formula; and a calculation unit 134 for calculating the corresponding compensation coefficient by substituting the numerator input source and the denominator input source selected by the numerator and denominator selecting unit into the following compensation coefficient calculation formula:

$$Factor_{compensation} = tabR(\text{Numerator})/tabR(\text{Denominator})$$

where tabR(Numerator) is a R coefficient value obtained by looking up a mapping table of a predetermined blood oxygen and R curve coefficient with the numerator input source being the blood oxygen value, and tabR(Denominator) is a R coefficient value obtained by looking up a mapping table of a predetermined blood oxygen and R curve coefficient with the denominator input source being the blood oxygen value; and $Factor_{compensation}$ is the complement coefficient.

For more details, reference may be made to the aforementioned description of FIG. 5.

The present disclosure further provides a system for calculating a physiological parameter, including:

a sensor comprising at least one light emitting tube and at least one receiving tube, the light emitting tube emitting at least two optical signals of different wavelengths for transmitting through a physiological tissue, and the receiving tube receiving the at least two optical signals transmitted through the physiological tissue and converting the at least two optical signals received into electrical signals;

an analog to digital converter connected to the sensor to convert the electrical signals into digital signals, the digital signals include at least some of the characteristics of the physiological tissue;

a digital processor connected to the analog to digital converter, wherein the digital processor executes the following processes:

performing a time-to-frequency domain transformation on a section of the digital signal to obtain a corresponding frequency domain signal;

selecting all rational frequency spectrum peaks from the frequency domain signal, calculating position information of the selected rational frequency spectrum peaks, and forming a frequency spectrum peak position sequence;

constructing a time-varying array map according to the frequency spectrum peak position sequence, and constructing at least one stability factor for each position point that varies over time to form a stability factor array map;

constructing a stability coefficient based on the stability factor array map, and if the stability coefficient is relatively low, calculating a compensation coefficient by using the stability factor array map; and compensating for at least one of the time domain signal and the frequency domain signal by using the compensation coefficient, and calculating the physiological parameter based on at least one of the compensated time domain signal and frequency domain signal.

Further, the system includes: a display unit connected to the digital processor to display the physiological parameter calculatied by the digital processor; and/or a communication unit connected to the digital processor to send the physiological parameter calculated by the digital processor.

In one embodiment, the two optical signals are red light and infrared light.

In one embodiment, the at least some of the characteristics of the physiological tissue is one or more of the optical characteristics of oxygenated hemoglobin, deoxyhemoglobin, methemoglobin, total hemoglobin and carbon monoxide in the blood.

In one embodiment, the rational frequency spectrum peaks satisfy at least one or more of a frequency spectrum energy relationship, a frequency spectrum amplitude relationship, a frequency spectrum positional relationship, and a frequency spectrum peak morphological relationship.

In one embodiment, the stability coefficient is constructed based on at least one of a frequency spectrum energy ratio deviation, a frequency spectrum blood oxygen deviation, a state of a fundamental and multiplied frequency group, a number of rational frequency spectrum peaks, and a frequency spectrum peak morphological rationality.

In one embodiment, the stability factor adjusts a stability weight thereof over time according to at least one of the characteristics of a fundamental and multiplied frequency group and a frequency spectrum peak morphological rationality.

In one embodiment, whether the stability coefficient is stable is determined according to at least one of a number of stability factors and weight values.

In one embodiment, the physiological parameter is at least one of blood oxygen, pulse rate, waveform area, perfusion index, etc.

For more details, reference may be made to the aforementioned description of FIG. 21; and, at the same time, in order to better understand the function and working principle of the digital processor in this embodiment, the following will be described in conjunction with a specific example.

Figure 10:
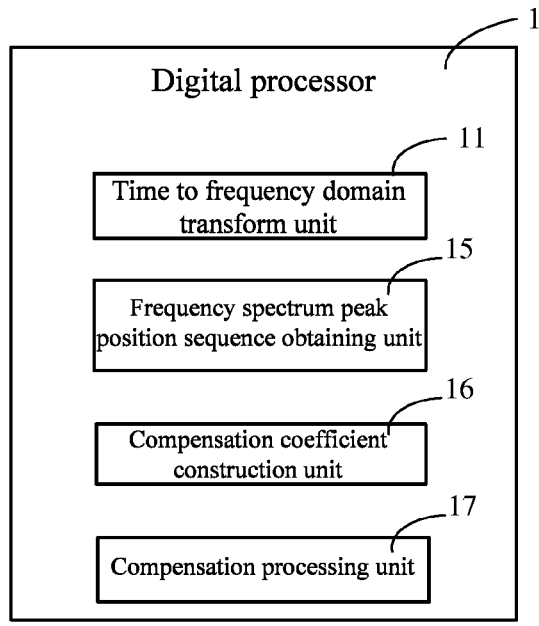
FIG. 10 is a schematic structural diagram of a digital processor used in a system for calculating a physiological parameter.
Figure 11:
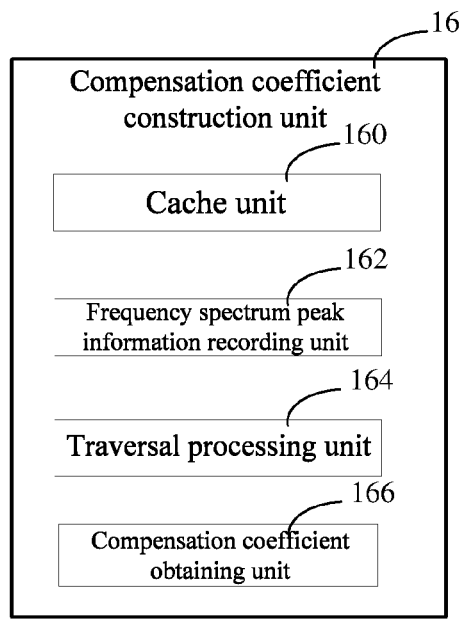
FIG. 11 is a schematic structural diagram of a compensation coefficient construction unit in FIG. 10.

As shown in FIG. 10, which shows a schematic structural diagram of a further embodiment of a digital processor used in a system for calculating a physiological parameter provided by the present disclosure, the digital processor uses a power spectrum array method (PSA) for compensation. Reference is also made to FIG. 11, in which digital processor is illustrated as including:

a time-to-frequency domain transformation unit 11 for selecting a section of a time domain signal corresponding to at least one signal of red light and infrared light obtained by sampling, and performing a time-to-frequency domain transformation on the section of the time domain signal to obtain at least one frequency domain signal;

a frequency spectrum peak position sequence obtaining unit 15 for selecting information about all rational frequency spectrum peaks from the frequency domain signal, calculating position information of the selected rational frequency spectrum peaks, and forming a frequency spectrum peak position sequence, wherein the information about the rational frequency spectrum peaks satisfies at least one or more of a frequency spectrum energy relationship, a frequency spectrum amplitude relationship, a frequency spectrum positional relationship, and a frequency spectrum peak morphological relationship;

a compensation coefficient construction unit 16 for constructing a stability coefficient according to the frequency spectrum peak position sequence, and if the stability coefficient is relatively low, constructing a time-varying array map according to the frequency spectrum peak position sequence, and calculating a compensation coefficient by means of the array map, wherein the stability coefficient is constructed based on at least one of a frequency spectrum energy ratio deviation, a frequency spectrum blood oxygen deviation, a state of a fundamental and multiplied frequency group, and a number of rational frequency spectrum peaks;

a compensation processing unit 17 for compensating for at least one of the time domain signal and the frequency domain signal by using the compensation coefficient, and calculating the physiological parameter based on at least one of the compensated time domain signal and frequency domain signal, wherein the physiological parameter is at least one of blood oxygen, pulse rate, waveform area, and perfusion index.

The compensation coefficient construction unit 16 may include:

a cache unit 160 for establishing a cache to store information about the frequency spectrum peaks, which information includes: each frequency spectrum peak position information; each frequency spectrum peak position weight information; and information about the number of frequency spectrum peaks stored;

a frequency spectrum peak information recording unit 162 for screening a predetermined number of frequency spectrum peaks in the frequency domain signal, sequentially filling same into the cache, writing the position information about each frequency spectrum peak, incrementing the corresponding position weight, and incrementing the total length quantity information;

a traversal processing unit 164 for, in the cache, assuming each frequency spectrum peak as a suspected fundamental frequency peak, traversing all the other frequency spectrum peaks, determining whether the other frequency spectrum peaks and the suspected fundamental frequency peak satisfy a frequency multiplication relationship, and if so, eliminating the information about the multiplied frequency peaks in the cache, and the position weight coefficients of the multiplied frequency peaks are converted according to the frequency multipliers and added to the position weight coefficient of the corresponding suspected fundamental frequency peak; otherwise, remaining the information about the other frequency spectrum peaks; and a compensation coefficient obtaining unit 166 for selecting three frequency spectrum peaks, position weight coefficients of which are ranked in the front in the last suspected frequency spectrum peak, determining one of them to be the final rational frequency spectrum peak, and using the information about the rational frequency spectrum peak as the compensation coefficient.

For more details, reference may be made to the aforementioned description of FIG. 6.

The present disclosure further provides a system for calculating a physiological parameter, including:

a sensor comprising at least one light emitting tube and at least one receiving tube, the light emitting tube emitting at least two optical signals of different wavelengths for transmitting through a physiological tissue, and the receiving tube receiving the at least two optical signals transmitted through the physiological tissue and converting the at least two optical signals received into electrical signals;

an analog to digital converter connected to the sensor to convert the electrical signals into digital signals, the digital signals include at least some of the characteristics of the physiological tissue;

a digital processor connected to the analog to digital converter, the digital processor performing the following processes:

performing a time-to-frequency domain transformation on a section of the digital signal to obtain a corresponding frequency domain signal;

selecting all rational frequency spectrum peaks from the frequency domain signal, calculating at least one of energy and position information of the selected rational frequency spectrum peaks, and forming at least one of a frequency spectrum peak energy ratio sequence and a frequency spectrum peak position sequence;

constructing a stability coefficient according to at least one of the frequency spectrum peak energy ratio sequence and the frequency spectrum peak position sequence, and if the stability coefficient is relatively low, constructing a compensation coefficient by using at least one of the frequency spectrum peak energy ratio sequence and the frequency spectrum peak position sequence; and compensating for at least one of the time domain signal and the frequency domain signal by using the compensation coefficient, and calculating the physiological parameter based on at least one of the compensated time domain signal and frequency domain signal.

In one embodiment, the two optical signals are red light and infrared light.

In one embodiment, the at least some of the characteristics of the physiological tissue is one or more of the optical characteristics of oxygenated hemoglobin, deoxyhemoglobin, methemoglobin, total hemoglobin and carbon monoxide in the blood.

In one embodiment, the rational frequency spectrum peaks satisfy at least one of a frequency spectrum energy relationship, a frequency spectrum amplitude relationship, a frequency spectrum positional relationship, and a frequency spectrum peak morphological relationship.

In one embodiment, the stability coefficient is constructed based on at least one of a frequency spectrum energy ratio deviation, a frequency spectrum blood oxygen deviation, a state of a fundamental and multiplied frequency group, and a number of rational frequency spectrum peaks.

In one embodiment, the compensation coefficient is an energy ratio deviation coefficient calculated based on the frequency spectrum peak energy ratio sequence, or a position coefficient statistically obtained over time based on the frequency spectrum peak position sequence.

In one embodiment, the process of compensating for at least one of the time domain signal and the frequency domain signal by using the compensation coefficient is specifically:

using the compensation coefficient to perform a gain processing on the selected time domain signal to achieve compensation; or using the compensation coefficient to perform filtering processing on the selected frequency domain signal to achieve compensation.

In one embodiment, the physiological parameter is at least one of blood oxygen, pulse rate, waveform area, perfusion index, etc.

For more details, reference may be made to the aforementioned description of FIG. 21; and at the same time, in order to better understand the function and working principle of the digital processor in this embodiment, the following will be described in conjunction with a specific example.

Figure 12:
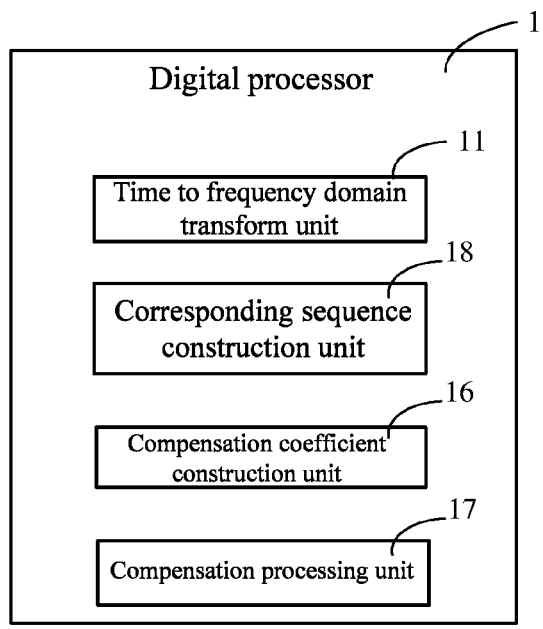
FIG. 12 is a schematic structural diagram of a a digital processor used in a system for calculating a physiological parameter.
Figure 13:
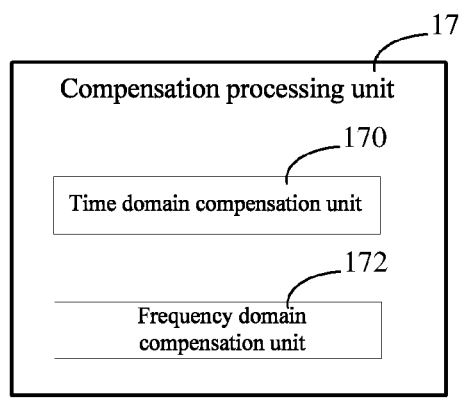
FIG. 13 is a schematic structural diagram of a compensation processing unit in FIG. 12.

As shown in FIG. 12, which shows a schematic structural diagram of a further embodiment of a digital processor used in a system for calculating a physiological parameter provided by the present disclosure, the digital processor uses a combined venous oxygen compensation (VOC) method and power spectrum array method (PSA) for compensation. Reference is also made to FIG. 13, specifically, in which the digital processor is illustrated to include:

a time-to-frequency domain transformation unit 11 for selecting a section of a time domain signal corresponding to at least one signal of red light and infrared light obtained by sampling, and performing a time-to-frequency domain transformation on the section of the time domain signal to obtain at least one frequency domain signal;

a corresponding sequence construction unit 18 for selecting information about all rational frequency spectrum peaks from the frequency domain signal, calculating at least one of energy and position information of the selected rational frequency spectrum peaks, and forming at least one of a frequency spectrum peak energy ratio sequence and a frequency spectrum peak position sequence, wherein the information about the rational frequency spectrum peaks satisfies at least one of a frequency spectrum energy relationship, a frequency spectrum amplitude relationship, a frequency spectrum positional relationship, and a frequency spectrum peak morphological relationship; and it will be understood that the corresponding sequence construction unit 18 has both the functions of the energy ratio sequence construction unit 13 in FIG. 8 and the frequency spectrum peak position sequence obtaining unit 15 in FIG. 10, and the specific details may be referred to the corresponding description above;

a compensation coefficient construction unit 16 for constructing a stability coefficient according to signal characteristics of at least one of the sequences, and at the same time, determining whether the stability coefficient of at least one of the sequences is relatively low, and if the stability coefficient is relatively low, constructing a compensation coefficient by using the signal characteristics of the at least one of the sequences, wherein the stability coefficient is constructed based on at least one of a frequency spectrum energy ratio deviation, a frequency spectrum blood oxygen deviation, a state of a fundamental and multiplied frequency group, and a number of rational frequency spectrum peaks; and the compensation coefficient construction unit 16 may construct the compensation coefficient based on an energy ratio deviation coefficient or a blood oxygen deviation coefficient calculated based on the frequency spectrum peak energy ratio sequence, or a position coefficient statistically obtained over time based on the frequency spectrum peak position sequence. It will be understood that the compensation coefficient construction unit 16 has both the functions of the compensation coefficient construction unit 16 in FIG. 8 and the compensation coefficient construction unit 16 in FIG. 10, and the specific details may be referred to the corresponding description above; and a compensation processing unit 17 for compensating for at least one of the time domain signal and the frequency domain signal by using the compensation coefficient, and further calculating the physiological parameter based on at least one of the compensated time domain signal and frequency domain signal, wherein the physiological parameter is at least one of blood oxygen, pulse rate, waveform area, and perfusion index.

The compensation processing unit 17 further includes:

a time domain compensation unit 170 for using the compensation coefficient to perform a gain processing on the selected time domain signal to achieve compensation; or a frequency domain compensation unit 172 for using the compensation coefficient to perform filtering processing on the selected frequency domain signal to achieve compensation.

For more details, reference may be made to the aforementioned description of FIG. 7.

In order to facilitate a better understanding of the present disclosure, the principles and implementation processes of the venous oxygen compensation (VOC) and power spectrum array (PSA) methods referred to in the foregoing will be further explained in conjunction with practical examples.

I. Venous Oxygen Compensation (VOC)

Under a non-interference condition, venous blood flows relatively slowly due to its physiological characteristics and may be considered as part of the direct current (DC) amount, and the venous blood oxygen saturation does not have any effect on the normal blood oxygen measurement. Under an interference condition, the venous blood is affected by the interference, a venous pulsation is generated, and the alternating current (AC) amount formed by the venous pulsation will be mixed into the AC amount formed by the arterial blood pulsation. According to Equation 1 described above, the oxygen saturation calculated at this point must deviate from the true value; from the physiological point of view, it will be understood that the venous blood oxygen saturation is mixed in the arterial blood oxygen saturation, resulting in that the final blood oxygen saturation deviates from a blood gas value.

Figure 14:
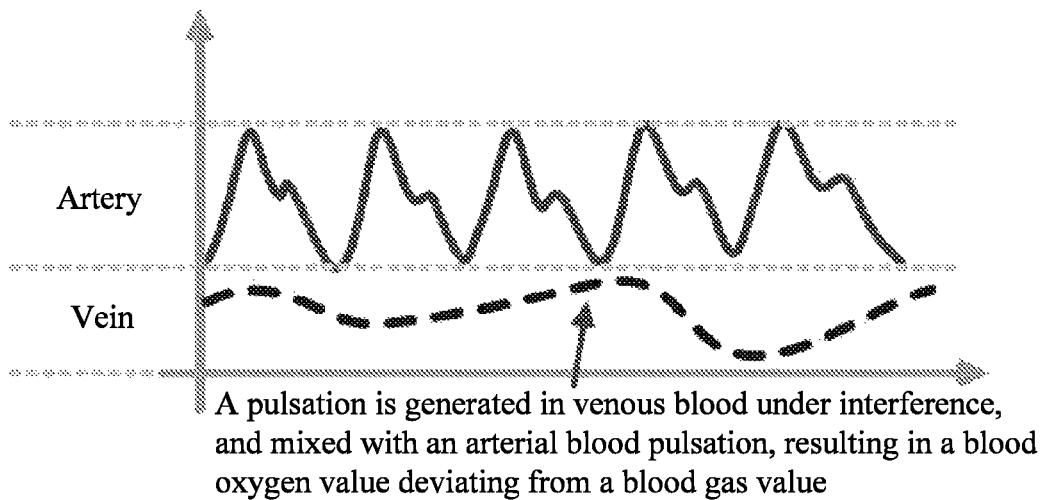
FIG. 14 is graph of a venous blood pulsation interfered with an arterial blood pulsation.
Figure 15:
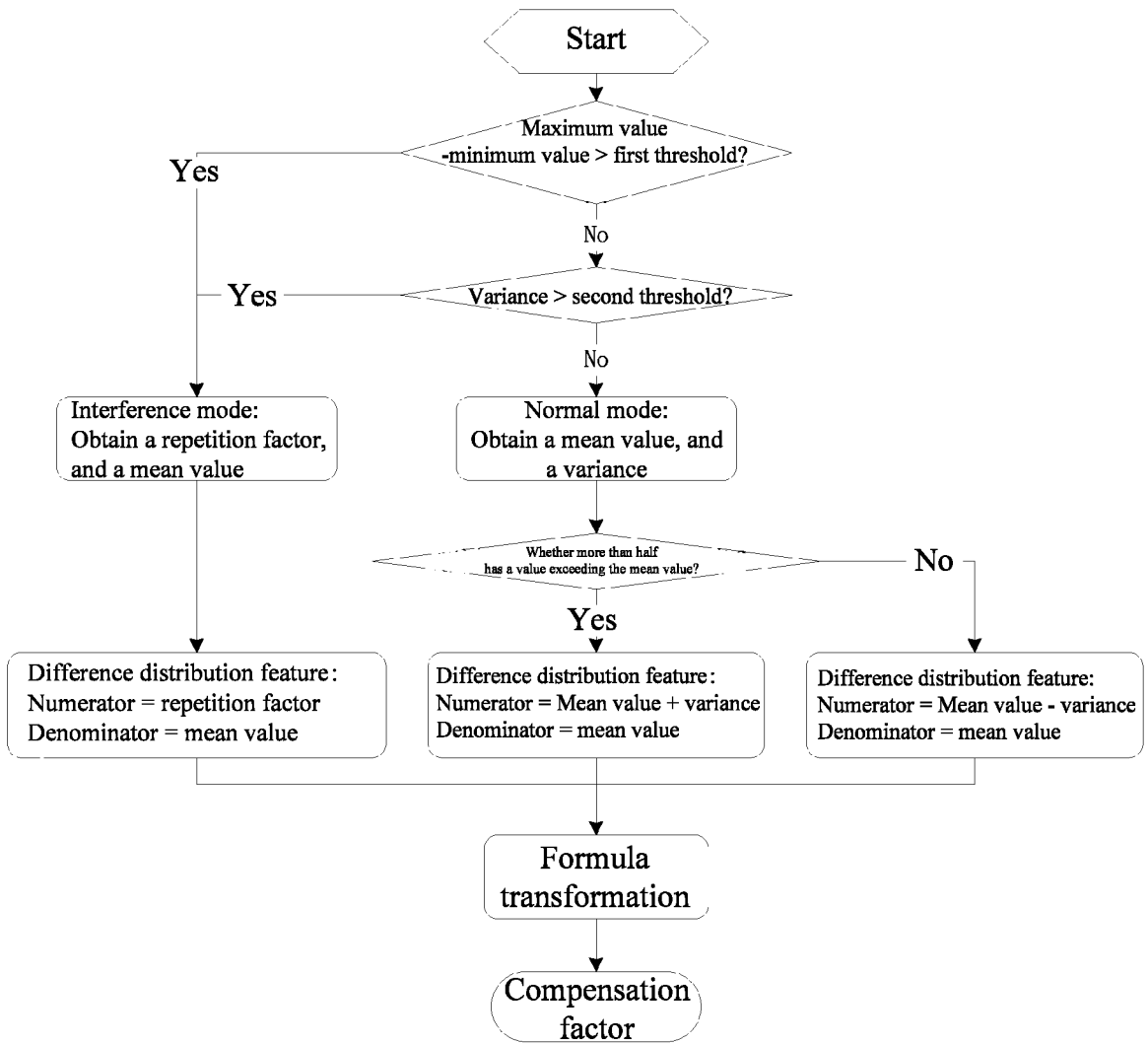
FIG. 15 is a flowchart of a process for calculating a compensation coefficient.

As shown in FIG. 14, a graph of a venous blood pulsation interfered with an arterial blood pulsation is given. In the case where random interference source characteristics may not be obtained, the time domain algorithm has almost no way to accurately calculate the blood oxygen saturation value; in addition, it is very difficult to obtain the random interference source characteristics.

Each frequency spectrum band in the frequency domain signal uniquely corresponds to the blood oxygen saturation. Theoretically, the blood oxygen saturation may be calculated for each frequency spectrum band; and due to the randomness of the venous interference, interferences superimposed on different frequency bands also have different weights. The venous oxygen compensation (VOC) method proposed in the present application is constructed based on the two hypothetical models. When the blood oxygen value deviation between the frequency spectrum bands is relatively large, it indicates that the venous pulsation has interfered with the real blood oxygen result, and a difference distribution feature is obtained by collecting and analyzing the change in the blood oxygen value deviations of the frequency spectrum bands, and based on this, the compensation coefficient is constructed to eliminate the interference in a blood oxygen sampling signal, and finally the parameter result infinitely approximating the true physiological blood oxygen may be obtained by recalculating the sampling signal with the interference eliminated.

Therefore, the process of the venous oxygen compensation (VOC) method may be as follows.

First, after the time-to-frequency domain transformation is completed, the difference between the blood oxygen saturations of the frequency spectrum bands in the frequency domain signal is statistically analyzed, thereby obtaining the difference distribution feature. That is, the frequency spectrum peaks that satisfy the condition are obtained from the frequency spectrum signal, and then the oxygen saturation of each frequency spectrum peak is calculated to obtain a blood oxygen saturation sequence. The frequency spectrum peaks satisfying the condition means that they are conform to the range of statistical analysis in terms of the amplitude, energy, width, and morphology. The determination criterion is established in accordance with the characteristics of the physiological signal and the basic method for processing a digital signal. Based on the blood oxygen saturation sequence, the mean value (vMean), the standard deviation (vStd), the maximum value (vMax), the minimum value (vMin), etc. of the blood oxygen are statistically obtained.

Second, the compensation coefficient calculation formula is constructed, and the compensation coefficient is calculated based on the difference distribution feature.

As shown in FIG. 13, a calculation process for the compensation coefficient is provided.

In a first step, the difference between vMax and vMin is compared with a first threshold (Threshold1), and the vStd value is compared with a second threshold (Threshold2) to determine whether a normal mode or an interference mode is selected. The first threshold and the second threshold are selected to be empirical coefficients obtained according to the characteristics of the physiological parameter and the characteristics of a blood oxygen system. For example, in an example, the first threshold (Threshold1) may be 15% of a blood oxygen deviation, and the second threshold (Threshold2) may be 5% of the blood oxygen deviation.

In a second step, if the normal mode is selected, it indicates that the fluctuation caused by the venous oxygen is relatively small, and the mean value and the standard deviation may be selected to be the input source of the compensation coefficient calculation formula. The mean value is used as the denominator input source, if the number of blood oxygens exceeding the mean value in the blood oxygen sequence accounts for at least half of the total number of the sequence, vMean+vStd is used as the numerator, otherwise, vMean−vStd is used as the numerator.

In a third step, which is alternative to the second step, if the abnormal mode is selected, it is necessary to introduce a repetition factor. There are two sources of repetition factors: 1) the maximum blood oxygen set, which satisfies a certain value (e.g., ±2%), in a blood oxygen sequence is collected and analyzed, and the mean value of the set is taken as the repetition factor, wherein ±2% here is an empirical coefficient which may be adjusted according to the actual change; and 2) a stable segment of the historical trend of the blood oxygen is selected, for example, the stable trend of 4 s-8 s, the mean value of the set is calculated as the repetition factor, and the time period of 4 s-8 s is also an empirical coefficient which may be adjusted according to the actual change. This repetition factor is used as the numerator input source, and the mean value is used as the denominator input source.

In a fourth step, the numerator and denominator parameters are input into Formula 2 below to calculate the compensation coefficient. The calculation formula is as follows, where tabR is a mapping table of blood oxygen and R curve coefficients (as described above), and the corresponding R coefficient values may be obtained by means of inverse look-up according to the input blood oxygen value. The compensation coefficient is the ratio of the R coefficient value of the numerator blood oxygen to the R coefficient value of the denominator blood oxygen.

$$\text{Factor}_{compensation} = \text{tab}R(\text{Numerator})/\text{tab}R(\text{Denominator}) \quad \text{Formula 2}$$

where $\text{Factor}_{compensation}$ is the compensation coefficient, tabR(Numerator) is the R coefficient value obtained by means of look-up after the numerator is used as the input source and substituted into the mapping table of blood oxygen and R curve coefficients, and tabR(Denominator) is the R coefficient value obtained by means of look-up after the denominator is used as the input source and substituted into the mapping table of blood oxygen and R curve coefficients.

Figure 16:
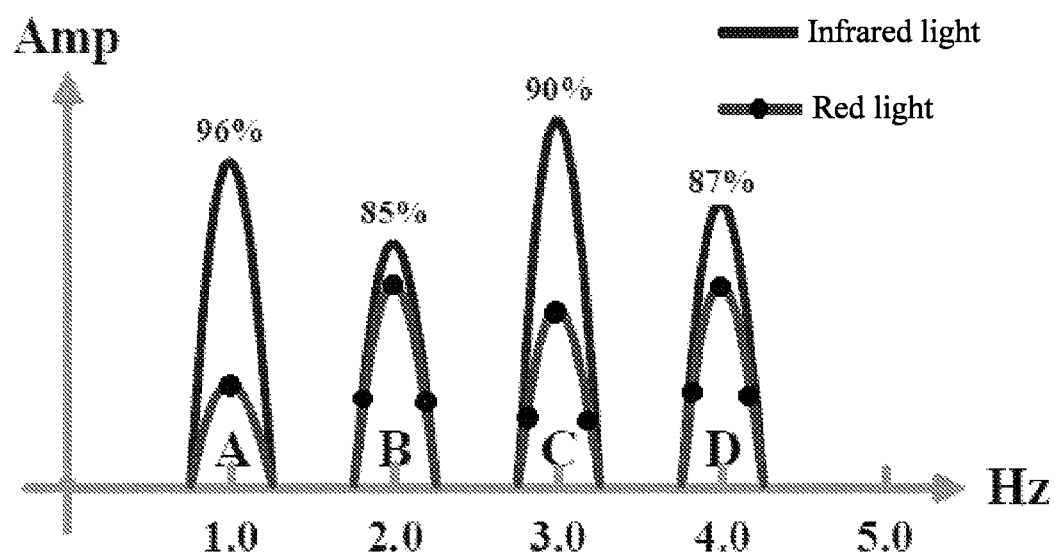
FIG. 16 is a graph of blood oxygen distribution in a frequency spectrum band under an interference condition.

The following will be combined with a practical example to illustrate how to calculate a compensation coefficient in the venous oxygen compensation (VOC) method. As shown in FIG. 16, a graph of blood oxygen distribution in a frequency spectrum band under an interference condition is given, assuming that the frequency spectrum signal has four frequency spectrum peaks A, B, C and D in a physiological bandwidth of 0.3 Hz-5 Hz, and assuming that the frequency spectrum signal is affected by a random pulsation of venous oxygen, and the oxygen saturation values of the frequency spectrum peaks obtained by converting the ratio of infrared light to red light are 96%, 85%, 90%, 87%, respectively. There is a deviation between the calculated values of the four blood oxygen saturation values. By collecting and analyzing the deviation distribution feature, the following may be respectively obtained: vMean=88.3%, vStd=4.8%, vMax=96%, and vMin=85%. It is determined that the deviation of vMax from vMin is less than the first threshold (e.g., 15%), and vStd is less than the second threshold (e.g., 5%), so the normal mode is selected. At this point, the number of blood oxygens exceeding the mean value is 2, accounting for 50% of the total blood oxygen sequence, so the numerator is selected as vMean+vStd=93.1%, and the denominator is vMean=88.3%. The R values corresponding to the numerator and the denominator are respectively obtained by looking up the mapping table of blood oxygen and R curve coefficients, and are substituted into Formula 2, so that a correction factor of about 1.172 may be calculated.

Again, the compensation coefficient is used to compensate for the loss of the time domain signal due to interference (the frequency domain signal is obtained by transforming this signal). That is, the time domain signal used for the frequency domain transformation is multiplied by the compensation coefficient to obtain a compensation signal. In an example of the present application, compensation is only made for the red light signal, as an example. However, in practical applications, the compensation coefficient may also be divided to achieve compensation for each signal.

Finally, the time domain signal that completes the compensation is used to be transformed to the frequency domain signal again, and then the frequency domain signal is used to calculate the accurate parameter such as blood oxygen. The embodiment of the present disclosure is an example given based on a frequency domain algorithm. In the actual application, the frequency domain method may also be omitted, and a time domain algorithm is used to obtain the accurate parameter such as blood oxygen based on the compensated time domain signal.

Figure 17:
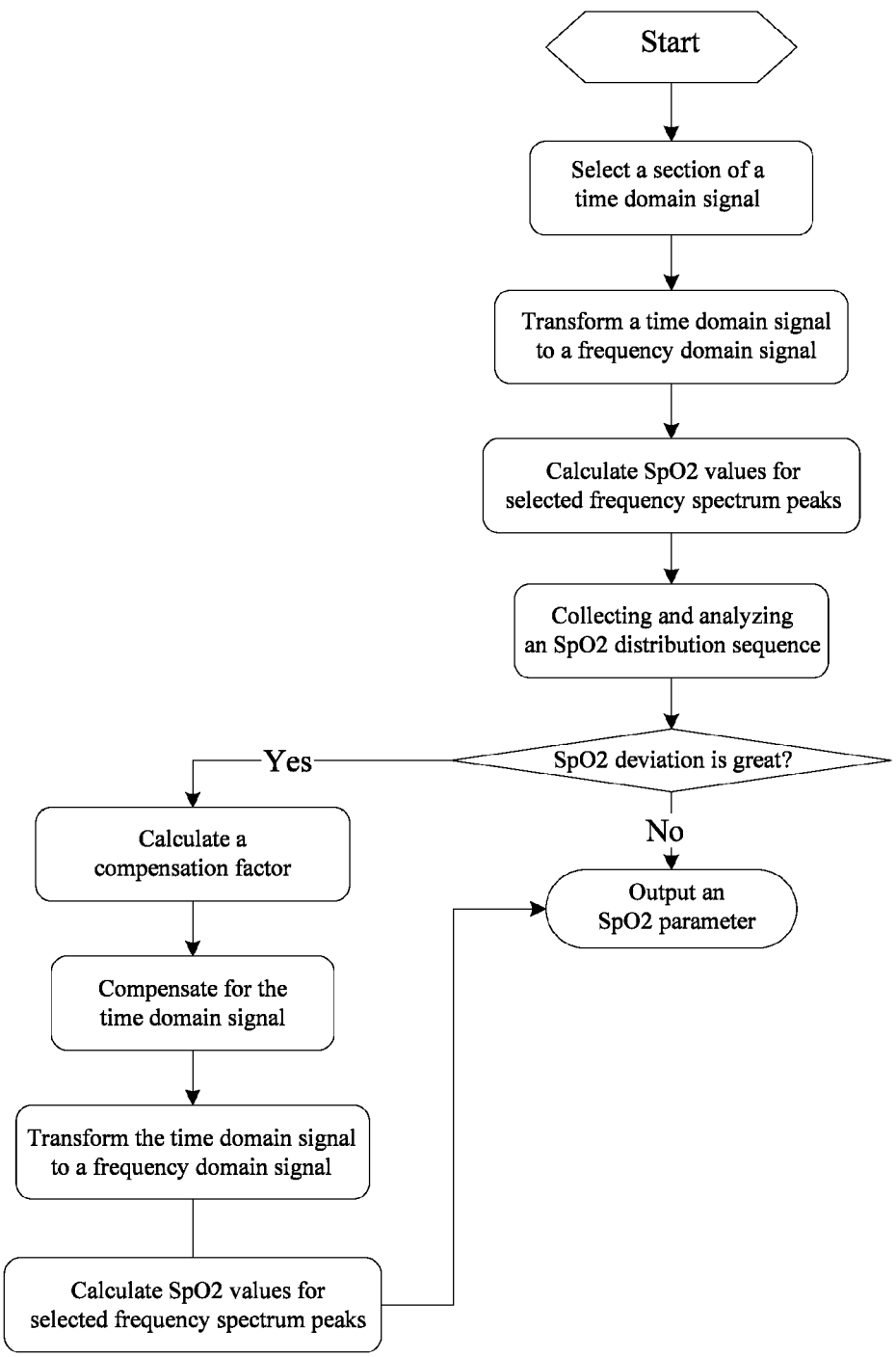
FIG. 17 is a flowchart of a venous oxygen compensation method.

As shown in FIG. 17, a flowchart of a venous oxygen compensation (VOC) method is given. The process may include: selecting a section of a time domain signal, and performing a time-to-frequency domain transformation on same to transform the time domain signal to a frequency domain signal. The characteristics of the physiological signal and the basic knowledge of digital signal processing (e.g., a physiological pulse wave frequency range, a fundamental and multiplied frequency principle, morphological features, etc.) are used, a rational frequency spectrum peak is selected and the blood oxygen saturation parameter of the frequency spectrum peak is calculated. According to the foregoing steps, a series of characteristic information is obtained by statistically analyzing a series of blood oxygen distribution, and according to the characteristic information, whether the blood oxygen saturations have a deviation (or a small deviation) is determined. If not, the result of the blood oxygen parameter is output; otherwise, the compensation coefficient is calculated based on the characteristic information and is compensated into the time domain signal. Finally, the compensated time domain signal is then used to re-perform a time-to-frequency domain transformation, the rational frequency spectrum peak is selected based on the new frequency domain signal, and the final blood oxygen saturation parameter is calculated and output.

It may be seen that the venous oxygen compensation (VOC) method may eliminate the measurement deviation of blood oxygenation caused by interference, infinitely approach the true physiological blood oxygen value, and greatly provide the accuracy of the calculation of the blood oxygen parameter under the interference condition.

II. Power Spectrum Array Method (PSA)

Figure 1:
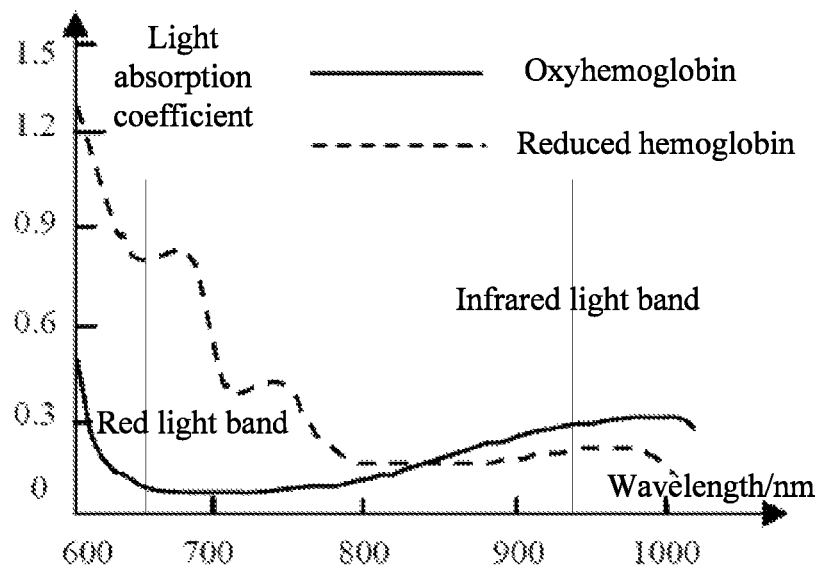
FIG. 1 is a graph showing absorption spectra of oxyhemoglobin and reduced hemoglobin.
Figure 2:
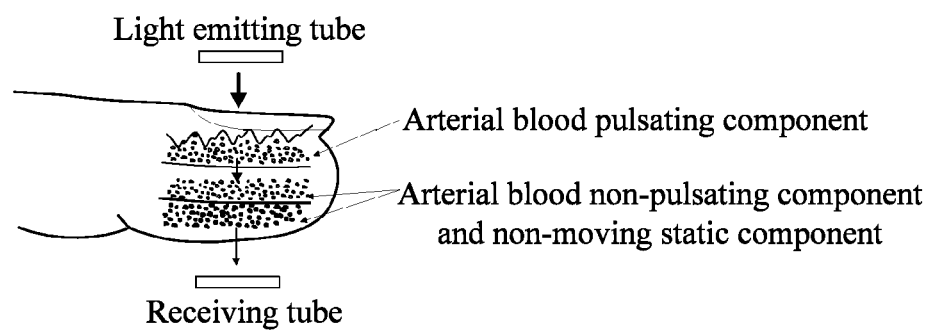
FIG. 2 is a diagram of blood oxygen measurement.
Figure 3:
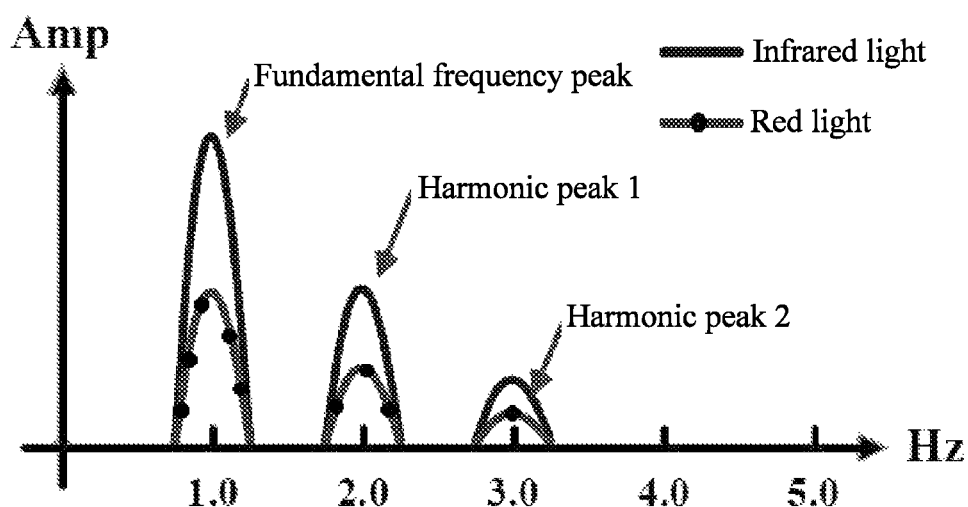
FIG. 3 is a frequency spectrum distribution diagram in the absence of interference.
Figure 4:
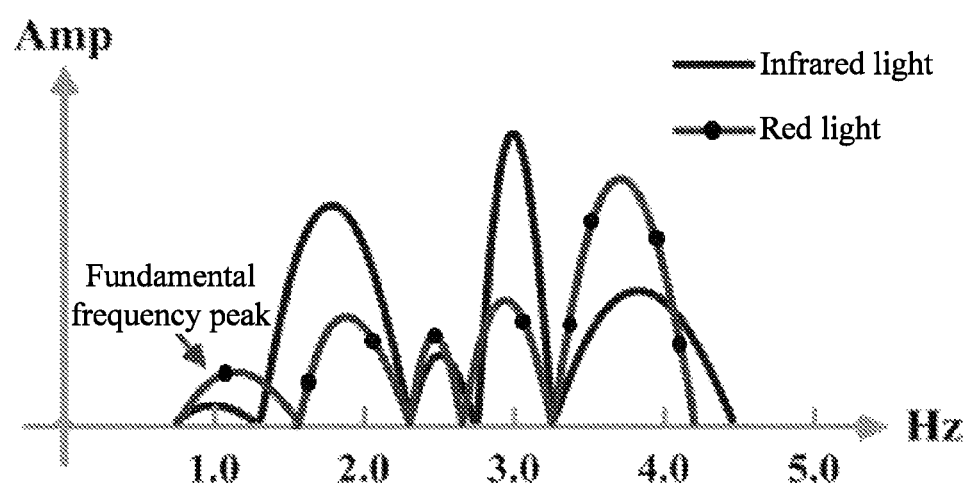
FIG. 4 is a frequency spectrum distribution diagram in the presence of interference.

When interference exists and severely disturbs the frequency spectrum signal, it is difficult to identify physiological frequency spectrum information from the frequency spectrum. For example, in the frequency spectrum diagram shown in FIG. 4, there is no way to identify the information about the fundamental peak based merely on the energy and frequency relationships of the fundamental and multiplied frequency principle. The task is to identify the physiological frequency spectrum peak under an interference condition. The present application proposes a hypothesis theory based on the characteristics of random distribution of noise. Any type of interference, such as weak perfusion, limb rubbing, finger shaking, etc., is presented as a random interference component in a blood oxygen sampling signal, and the intensity of the interference is positively correlated with the intensity of movement of the measuring end.

Considering the state of the physiological characteristics, most of the interferences are presented as random white noise distribution; and a few thereof are relatively regular interferences (e.g., Parkinson's disease), because of the relatively low amplitude of vibration, the vibration frequency is relatively high, but has no substantial effect on the blood oxygen sampling signal, that is, does not affect the measurement of the blood oxygen parameter. Although the interference signal disturbs the frequency spectrum signal such that the physiological frequency spectrum may not be recognized, no matter how the interference signal changes, the characteristics of the physiological frequency spectrum peak always exist at a certain frequency point and will not change or change slowly in a certain period of time (the physiological characteristics); and at the same time, the interference noise is randomly distributed, and the characteristics of the frequency spectrum change over time.

By arranging the frequency spectrum at each moment in chronological order and observing the characteristics of the frequency spectrum signal longitudinally, it may be found that when the amplitudes and positions of most of the frequency spectrum peaks change, there is always at least one frequency spectrum peak, the position of which is relatively stable and does not shift. This frequency spectrum peak is the physiological frequency spectrum peak (fundamental frequency peak). If an identification algorithm may be used to find the frequency spectrum peak, it means that the correct pulse rate value is found. This is the core idea of the power spectrum array method.

In the present application, the general process of the power spectrum array (PSA) method is as follows.

First, a cache is established to store information about the frequency spectrum peaks. For example, frequency spectrum peak position information, that is, the currently-located frequency point (PeakArray); frequency spectrum peak position weight information (WeigtedArray); and information about the number of frequency spectrum peaks stored (ArrayIndex), wherein the position information and the weight information share the number information. In general, the number of frequency spectrum peaks examined should not be too large. Too many frequency spectrum peaks will increase the complexity and computational complexity of the algorithm identification. For example, 20 may be selected as the upper limit by default, beyond which the analysis would not be carried out. It will be understood that in practical applications, the appropriate number of analysis may also be selected according to the requirements of the system.

Second, rational frequency spectrum peaks are screened from the frequency domain signal and are filled into the above cache. The criteria for screening are based on a combination of information such as the energy, amplitude, shape, and position of the frequency spectrum peak. When recording the information, the position information about the frequency spectrum peak is written into the PeakArray, the corresponding position weight in the WeigtedArray is incremented, and the total length ArrayIndex is incremented.

By analogy, all the frequency spectrum peaks identified by one calculation are added into the cache. If information recording occurs 2 times, there is a need to consider whether the frequency spectrum peak to be added is already stored in the cache. If it exists, the corresponding position weight of the WeigtedArray is incremented, otherwise the new frequency spectrum peak is added in the conventional manner. Assuming that each calculation interval is 2 S, the cache needs to accumulate frequency spectrum information for a certain period of time before the identification of the physiological frequency spectrum peak may be initiated. This time needs to be set according to the actual requirements of the system. For example, it may be set to 10 times of calculations, that is, the time trend of 20 S. When 10 times of information storage is satisfied, the relevant trend analysis is started, and after the trend analysis is completed, the earliest stored frequency spectrum information is reduced.

Again, the true physiological frequency spectrum peak is identified according to the information about the cache. According to the fundamental and multiplied frequency principle, the multiplied frequency peaks in the PeakArray are eliminated; at the same time, the weight coefficients of the multiplied frequency peaks are converted according to the frequency multipliers and added to the weight coefficient of the fundamental frequency peak (for example, the fundamental frequency peak weight coefficient is 3, the weight coefficient of a 2-multiplied frequency peak is 2, the weight coefficient of 2 is divided by the frequency multiplier of 2 to obtain the adjusted weight coefficient of 1, which is added to the weight coefficient of the fundamental frequency peak, that is, the weight coefficient of the fundamental frequency peak is adjusted to 4), and the information about the multiplied frequency stored in the PeakArray and WeigtedArray is eliminated, i.e., is initialized to 0.

Figure 18:
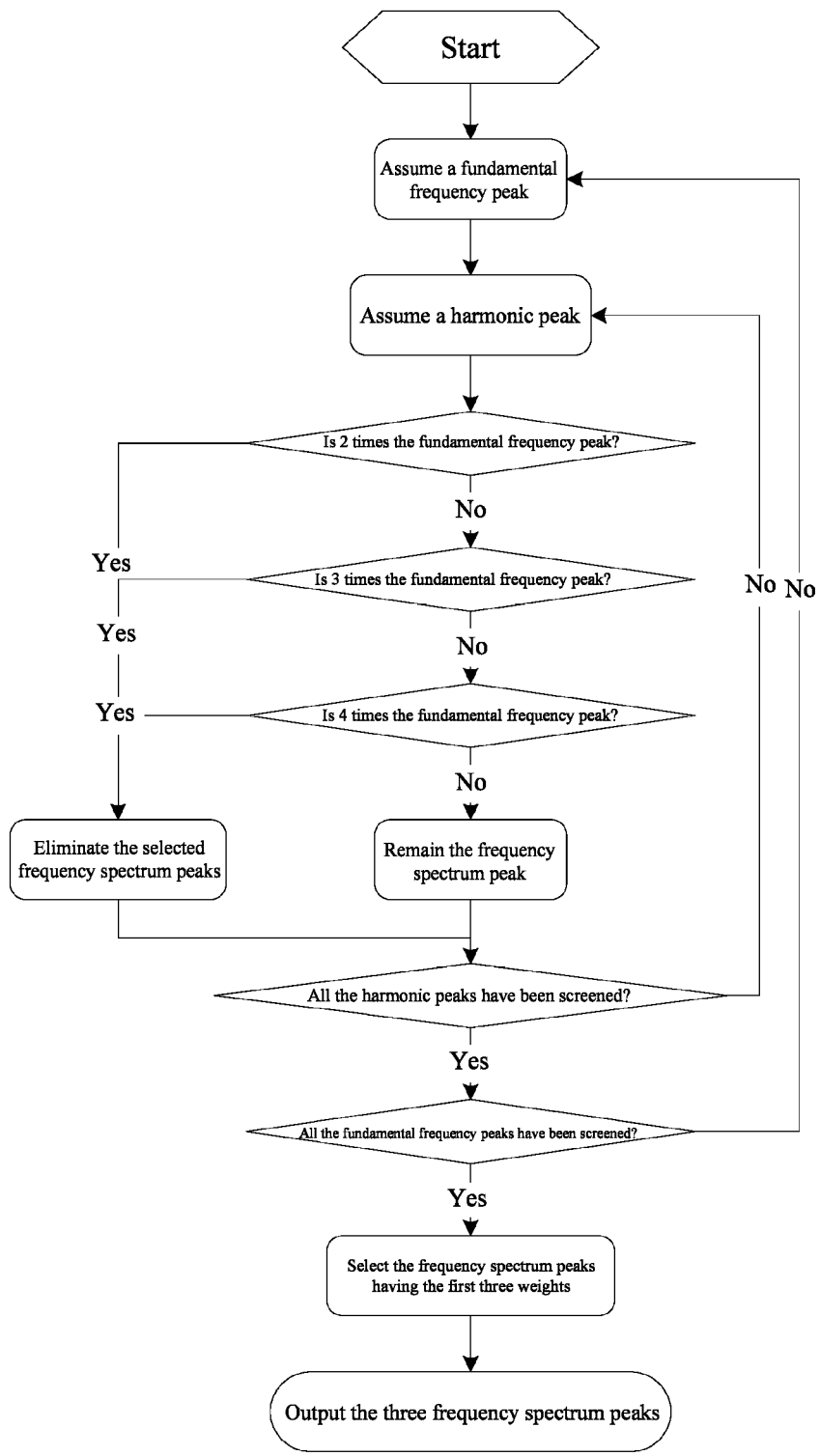
FIG. 18 is a flowchart of a screening process of the fundamental and multiplied frequencies.

The detailed process is as shown in FIG. 18, at this point, it may be assumed that each frequency spectrum peak is the fundamental frequency peak, all the other frequency spectrum peaks are traversed, and it is determined whether the other frequency spectrum peaks and the assumed fundamental frequency peak satisfy a frequency multiplication relationship, and if so, the information about the multiplied frequency peaks is eliminated; otherwise, remaining the information.

According to the characteristics of the energy attenuation of the fundamental and multiplied frequencies, and the physiological characteristics, in general, the influence of the multiplied frequency having a multiplier more than 4 is relatively small, which may be selected and set according to the requirements of the system in practical applications. Following a similar operation, each frequency spectrum peak is traversed, to complete the elimination of the information about the multiplied frequency peaks. Finally, the peaks with the first three largest weight coefficients are selected as the input information for the next step.

Finally, it is determined whether the maximum weight coefficient of the frequency spectrum peak is greater than or equal to a set threshold (for example, the threshold may be set to be 8, indicating that there is a stable frequency spectrum peak for 16 s consecutively, which may be selected and set according to the requirements of the system in practical applications). If two or more frequency spectrum peaks satisfy the weight coefficient greater than or equal to the set threshold, there is a need to further make a determination based on the physiological characteristics. For example, under an interference condition, the physiological pulse rate may not be too high and may not be relatively low. The most rational frequency spectrum peak that satisfies the set threshold is selected, the pulse rate parameter is calculated and output, and the weight coefficients of the other frequency spectrum peaks are optimized according to the state at the same time.

Figure 19:
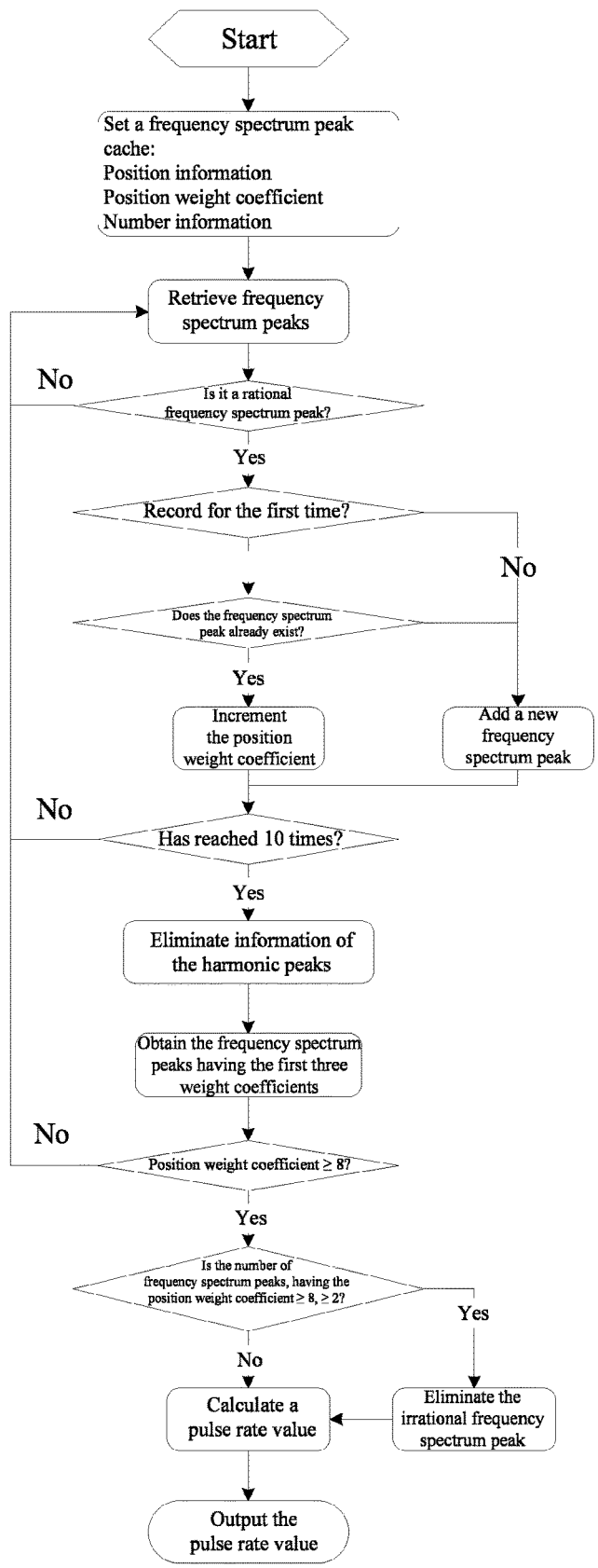
FIG. 19 is flowchart of a power spectrum array method.

As shown in FIG. 19, a flowchart of a power spectrum array (PSA) method is given. It may be seen that the frequency spectrum peak information cache is first established, and the cache is filled in chronological order. When the cache is filled up, the stored frequency spectrum peaks are simplified according to the fundamental and multiplied frequency principle, and the frequency spectrum peaks that satisfy the set threshold are selected from the simplified frequency spectrum peaks. If the number of frequency spectrum peaks that satisfy the condition is greater than or equal to two, an exclusion operation is performed on same according to the criterion of converting the physiological characteristics, and finally one rational frequency spectrum peak is selected, and the pulse rate parameter is calculated based on this frequency spectrum peak. The power spectrum array (PSA) method may eliminate the measurement deviation of the pulse rate caused by interference, may accurately identify the physiological frequency spectrum information even under the long-term interference condition, and greatly provides the accuracy of the calculation of the pulse rate parameter under the interference condition.

In summary, the venous oxygen correction (VOC) method may identify the interference of venous oxygen and compensate for the blood oxygen deviation caused by the interference, and the power spectrum array (PSA) method may accurately identify the pulse rate information in a continuous interference. Each of the two methods has the ability to identify and process the interference. Therefore, when the two methods are combined, the identification and suppression of the interference may be significantly improved, thereby obtaining the great improvement in the accuracy of the calculation of the blood oxygen parameter and the accuracy of the pulse rate parameter.

Figure 20:
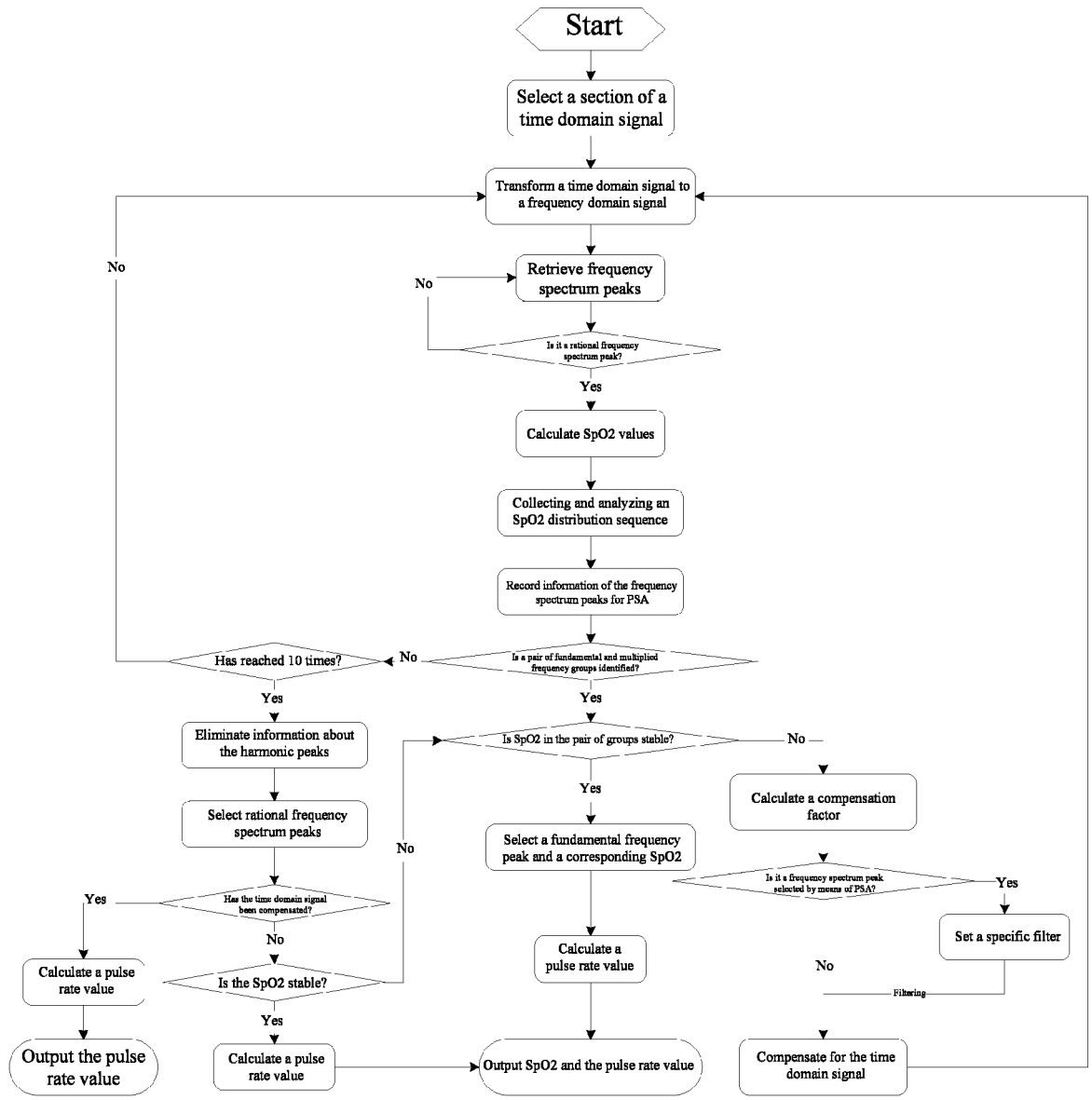
FIG. 20 is a schematic diagram of a process using both the venous oxygen compensation method and the power spectrum array method of an embodiment of the present disclosure.

As shown in FIG. 20, an example of the combined application of the two solutions in the method provided by the present disclosure is shown. In practical applications, these steps may be adaptively added, deleted, and adjusted according to the requirements of the system.

The general process is as follows: selecting a specified section of a time domain signal, performing a time-to-frequency transformation on same, and perform a retrieval and identification on frequency spectrum peaks based on the transformed frequency spectrum signal, and calculating a blood oxygen value of each rational frequency spectrum peak at the same time. The blood oxygen values of the rational peaks are collected and analyzed to obtain relevant statistical information to prepare for the VOC, and the information about all the frequency spectrum peaks obtained by the current calculation is also recorded to prepared for the PSA.

If a pair of fundamental and multiplied frequency groups are identified and the relative deviation of the blood oxygen values of the frequency spectrum peaks is relatively small, the fundamental frequency peak is directly selected to calculate the pulse rate, and the finally resulting blood oxygen and pulse rate values are output. If the pair of fundamental and multiplied frequency groups is not satisfied, the PSA method is implemented, and the rational frequency spectrum peak is calculated.

If the time domain signal with the noise/compensated venous oxygen being eliminated is based, but the blood oxygen value is unstable (for example, it does not match the historical trend result), only the pulse rate parameter is calculated and output; otherwise, if the blood oxygen value is stable, the pulse rate value is calculated, and the finally resulting blood oxygen and pulse rate values are output; if the first calculation is performed (the noise/compensated venous oxygen is not eliminated from the time domain signal) and the blood oxygen value is unstable, a VOC identification branch is implemented.

A specific filter of the frequency spectrum peaks obtained based on the PSA method is added to the VOC identification branch. Combining the compensation coefficient with the specific filter, the time domain signal is compensated and the noise is eliminated, and then the time-to-frequency domain transformation is performed again and the relevant parameter is calculated.

In summary, the methods and the system provided in the embodiments of the present disclosure have the following beneficial effects.

First, the embodiments of the present disclosure are based on the frequency domain technology combined with the time domain technology, may greatly improve the calculation accuracy of the blood oxygen and pulse rate parameters under weak perfusion and movement states, bring a client an excellent clinical performance experience, and may greatly improve the application and promotion of the blood oxygen parameter;

Second, the present disclosure is implemented by combining the characteristics of time and frequency domain signals with the characteristics of the human physiological parameter, the venous oxygen compensation method and the power spectrum array method are used in the case of interference, so as to improve the accuracy of calculating the pulse rate value and the blood oxygen parameter under weak irrigation and movement conditions. The venous oxygen compensation method may eliminate the measurement deviation of blood oxygenation caused by interference, infinitely approach the true physiological blood oxygen value, and greatly provide the accuracy of the calculation of the blood oxygen parameter under the interference condition. The power spectrum array method may eliminate the measurement deviation of the pulse rate caused by interference, may accurately identify the physiological frequency spectrum information even under the long-term interference condition, and greatly provides the accuracy of the calculation of the pulse rate parameter under the interference condition.

In addition, the methods provided in the embodiments of the present disclosure have low computational complexity and low demand for computing resources.

Those skilled in the art may understand that the implementation of all or part of the steps in the methods of the above embodiments may be implemented by a program to instruct related hardware. The program may be stored in a computer readable storage medium, such as a ROM/RAM, a magnetic disk, an optical disc, etc.

The above are only the preferred embodiments of the present disclosure, and are not intended to limit the present disclosure. Any modifications, equivalents, and improvements made within the spirit and principles of the present disclosure should be included in the scope of the present disclosure.

What is claimed is:

1. A method for calculating a physiological parameter, comprising:
   selecting a section of a time domain signal corresponding to at least one signal of red light and infrared light obtained by sampling, and performing a time-to-frequency domain transformation on the section of the time domain signal to obtain a corresponding frequency domain signal;
   selecting all rational frequency spectrum peaks from the frequency domain signal, calculating energy information of the selected rational frequency spectrum peaks, and forming a frequency spectrum peak energy ratio sequence;
   constructing a stability coefficient according to the frequency spectrum peak energy ratio sequence, and if the stability coefficient is relatively low, constructing a compensation coefficient by using the frequency spectrum peak energy ratio sequence; wherein constructing the compensation coefficient comprises selecting a mean value of a statistical spectrum peak energy ratio deviation sequence and converting same by means of a coefficient table to a denominator of a compensation coefficient calculation formula, and selecting either the mean value plus the standard deviation or the mean value minus the standard deviation and converting same by means of a coefficient table to a numerator of the compensation coefficient calculation formula, and calculating a ratio of the numerator to the denominator to obtain the compensation coefficient; and
   compensating for at least one of the time domain signal and the frequency domain signal by using the compensation coefficient, and calculating the physiological parameter based on at least one of the compensated time domain signal and frequency domain signal.

2. The method of claim 1, wherein the rational frequency spectrum peaks satisfy at least one of a frequency spectrum energy relationship, a frequency spectrum amplitude relationship, a frequency spectrum positional relationship, and a frequency spectrum peak morphological relationship.

3. The method of claim 1, wherein the stability coefficient is constructed based on deviation statistics for energy ratios of the red light and the infrared light, or is an empirical coefficient; and
   if the stability coefficient is less than or equal to a set threshold, the stability coefficient is determined to be relatively low.

4. The method of claim 3, wherein the step of constructing the stability coefficient according to the frequency spectrum peak energy ratio sequence comprises: constructing the stability coefficient according to a predetermined algorithm by using information about a mean value, a standard deviation, a maximum value, and a minimum value of a statistical spectrum peak energy ratio deviation sequence.

5. The method of claim 4, wherein the physiological parameter is at least one of blood oxygen, pulse rate, waveform area, and perfusion index.

6. A method for calculating a physiological parameter, comprising:
   selecting a section of a time domain signal corresponding to at least one signal of red light and infrared light obtained by sampling, and performing a time-to-frequency domain transformation on the section of the time domain signal to obtain at least one frequency domain signal;
   selecting all rational frequency spectrum peaks from the frequency domain signal, calculating position information of the selected rational frequency spectrum peaks, and forming a frequency spectrum peak position sequence;
   constructing a time-varying array map according to the frequency spectrum peak position sequence, and constructing at least one stability factor for each position point that varies over time to form a stability factor array map;
   constructing a stability coefficient based on the stability factor array map, and if the stability coefficient is relatively low, calculating a compensation coefficient by using the stability factor array map; wherein at least one frequency spectrum peak with a highest weight is selected from the stability factors, and is combined with at least one of frequency characteristics and frequency spectrum peak morphological features to calculate the compensation coefficient; and compensating for at least one of the time domain signal and the frequency domain signal by using the compensation coefficient, and calculating the physiological parameter based on at least one of the compensated time domain signal and frequency domain signal.

7. The method of claim 6, wherein the rational frequency spectrum peaks satisfy at least one or more of a frequency spectrum energy relationship, a frequency spectrum amplitude relationship, a frequency spectrum positional relationship, and a frequency spectrum peak morphological relationship.

8. The method of claim 6, wherein the stability coefficient is constructed based on at least one of a frequency spectrum energy ratio deviation, a frequency spectrum blood oxygen deviation, a state of a fundamental and multiplied frequency group, a number of rational frequency spectrum peaks, and a frequency spectrum peak morphological rationality.

9. The method of claim 6, wherein the stability factor adjusts a stability weight thereof over time according to at least one of the characteristics of a fundamental and multiplied frequency group and a frequency spectrum peak morphological rationality.

10. The method of claim 9, further comprising determining whether the stability coefficient is relatively low according to at least one of a number of stability factors and weight values.

11. The method of claim 6, wherein the physiological parameter is at least one of blood oxygen, pulse rate, waveform area, and perfusion index.

12. A system for calculating a physiological parameter, comprising:

a sensor comprising at least one light emitting tube and at least one receiving tube, the light emitting tube emitting at least two optical signals of different wavelengths for transmitting through a physiological tissue, and the receiving tube receiving the at least two optical signals transmitted through the physiological tissue and converting the at least two optical signals received into electrical signals;

an analog to digital converter connected to the sensor to convert the electrical signals into digital signals, the digital signals include at least some characteristics of the physiological tissue; and a digital processor connected to the analog to digital converter, the digital processor performing the following processes:

performing a time-to-frequency domain transformation on a section of the digital signal to obtain a corresponding frequency domain signal;

selecting all rational frequency spectrum peaks from the frequency domain signal, calculating energy and position information of the selected rational frequency spectrum peaks, and forming a frequency spectrum peak energy ratio sequence and a frequency spectrum peak position sequence;

constructing a stability coefficient according to the frequency spectrum peak energy ratio sequence and the frequency spectrum peak position sequence, and if the stability coefficient is relatively low, constructing a compensation coefficient by using the frequency spectrum peak energy ratio sequence and the frequency spectrum peak position sequence; and compensating for at least one of the time domain signal and the frequency domain signal by using the compensation coefficient, and calculating the physiological parameter based on at least one of the compensated digital signal and frequency domain signal.

13. The system of claim 12, wherein the at least some of the characteristics of the physiological tissue is one or more of the optical characteristics of oxygenated hemoglobin, deoxyhemoglobin, methemoglobin, total hemoglobin and carbon monoxide in the blood.

14. The system of claim 12, wherein the rational frequency spectrum peaks satisfy at least one of a frequency spectrum energy relationship, a frequency spectrum amplitude relationship, a frequency spectrum positional relationship, and a frequency spectrum peak morphological relationship.

15. The system of claim 12, wherein the stability coefficient is constructed based on at least one of a frequency spectrum energy ratio deviation, a frequency spectrum blood oxygen deviation, a state of a fundamental and multiplied frequency group, and a number of rational frequency spectrum peaks.

16. The system of claim 12, wherein the compensation coefficient is an energy ratio deviation coefficient calculated based on the frequency spectrum peak energy ratio sequence, or a position coefficient statistically obtained over time based on the frequency spectrum peak position sequence.

17. The system of claim 15, wherein the process of compensating for at least one of the time domain signal and the frequency domain signal by using the compensation coefficient comprises:

using the compensation coefficient to perform a gain processing on the selected time domain signal to achieve compensation; or using the compensation coefficient to perform filtering processing on the selected frequency domain signal to achieve compensation.

18. The system of claim 12, wherein the physiological parameter is at least one of blood oxygen, pulse rate, waveform area, and perfusion index.

* * * * *

UNITED STATES PATENT AND TRADEMARK OFFICE
CERTIFICATE OF CORRECTION

PATENT NO.       : 11,154,250 B2
APPLICATION NO.  : 16/203068
DATED            : October 26, 2021
INVENTOR(S)      : Fei Han et al.

It is certified that error appears in the above-identified patent and that said Letters Patent is hereby corrected as shown below:

On the Title Page

In Item (72), add the following inventor to the indicated Inventors information:
- Xingliang JIN, Shenzhen (CN) -

Signed and Sealed this
Thirty-first Day of January, 2023

Katherine Kelly Vidal
*Director of the United States Patent and Trademark Office*